US008569001B2

(12) United States Patent
Okamura et al.

(10) Patent No.: US 8,569,001 B2
(45) Date of Patent: Oct. 29, 2013

(54) METHOD FOR DETECTING LYSOSOMAL STORAGE DISEASES

(75) Inventors: Kazuo Okamura, Saitama (JP); Shuichi Miyaura, Kanagawa (JP); Shunji Tomatsu, Clayton, MO (US)

(73) Assignees: Seikagaku Corporation, Tokyo (JP); Saint Louis University, St. Louis, MO (US)

( * ) Notice: Subject to any disclaimer, the term of this patent is extended or adjusted under 35 U.S.C. 154(b) by 0 days.

(21) Appl. No.: 13/091,752

(22) Filed: Apr. 21, 2011

(65) Prior Publication Data

US 2011/0256563 A1    Oct. 20, 2011

Related U.S. Application Data

(63) Continuation of application No. 10/512,839, filed as application No. PCT/US03/13517 on Apr. 30, 2003, now Pat. No. 7,951,545.

(60) Provisional application No. 60/441,325, filed on Jan. 22, 2003, provisional application No. 60/376,194, filed on Apr. 30, 2002.

(51) Int. Cl.
*G01N 33/00* (2013.01)

(52) U.S. Cl.
CPC ..................................... *G01N 33/00* (2013.01)
USPC ......... 435/7.92; 435/7.1; 435/7.93; 435/7.94; 436/501; 436/518

(58) Field of Classification Search
None
See application file for complete search history.

(56) References Cited

U.S. PATENT DOCUMENTS

| | | | |
|---|---|---|---|
| 4,704,356 A | 11/1987 | Thonar | |
| 5,185,245 A | 2/1993 | Heimer | |
| 5,310,646 A | 5/1994 | Whitley | |
| 6,291,439 B1 * | 9/2001 | Klock | ............................. 514/56 |
| 2003/0157580 A1 | 8/2003 | Hochstrasser et al. | |
| 2007/0161074 A1 | 7/2007 | Tomatsu et al. | |
| 2009/0280505 A1 | 11/2009 | Okamura et al. | |
| 2011/0008810 A1 | 1/2011 | Tomatsu et al. | |

FOREIGN PATENT DOCUMENTS

| | | |
|---|---|---|
| EP | 0 869 362 A2 | 10/1998 |
| JP | 10-153600 | 9/1998 |
| WO | WO 01/94941 A2 | 2/2001 |
| WO | WO 03/106997 A1 | 12/2003 |

OTHER PUBLICATIONS

Iwata et al., Letters to the Editor, Glcosaminoglycans in neonatal urine, Arch Dis Child Fetal neonatal Ed 2000; 82: pp. F77-F78.*

Starr et al., Fluorophore-assisted electrophoresis of urinary carbohydrates for the identification of patients with oligosaccharidosis- and mucopolysaccharidosis-type lysosomal storage diseases, Glycosylation & Disease, 1994, 1, pp. 165-176.*
European Office Action issued Sep. 16, 2010, in Patent Application No. 03 724 355.7.
Office Action mailed Jul. 16, 2009 in co-pending U.S. Appl. No. 11/616,586.
C. A. Pennock, "A review and selection of simple laboratory methods used for the study of glycosaminoglycan excretion and the diagnosis of the mucopolysaccharidoses" J. Clin. Path., vol. 29, 1976, pp. 111-123.
John J. Hopwood, et al., "High-Resolution Electrophoresis of Urinary Glycosaminoglycans: An Improved Screening Test for the Mucopolysaccharidoses", Analytical Biochemistry, vol. 119, Jan. 1, 1982, pp. 120-127.
S. Byers, et al., "Glycosaminoglycan Accumulation and Excretion in the Mucopolysaccharidoses: Characterization and Basis of a Diagnostic Test for MPS", Molecular Genetics and Metabolism, vol. 65, No. 4, Jan. 1, 1998, pp. 282-290.
Margaret Z. Jones, et al., "Human Mucopolysaccharidosis IIID: Clinical, Biochemical, Morphological and Immunohistochemical Characteristics", Journal of Neuropathology and Experimental Neurology, vol. 56, No. 10, Oct. 1997, pp. 1158-1167.
Akira Mada, et al., "Utility of a Carbon Column For High-Performance Liquid Chromatographic Separation of Unsaturated Disaccharides Produced from Glycosaminoglycans", Analytical Sciences, vol. 8, Dec. 1992, pp. 793-797.
Toshihiro Oguma, et al., "Analytical method of chondroitin/dermatan sulfates using high performance liquid chromatography/turbo ionspray ionization mass spectrometry: application to analyses of the tumor tissue sections on glass slides", Biomedical Chromatography, vol. 15, 2001, pp. 356-362.
Toshihiro Oguma, et al., "Analytical Method for Keratan Sulfates by High-Performance Liquid Chromatography/Turboionspray Tandem Mass Spectrometry", Analytical Biochemistry, vol. 290, 2001, pp. 68-73.
Toshihiro Oguma, et al., "Analytical method of heparan sulfates using high-performance liquid chromatography turboionspray ionization tandem mass spectrometry", Journal of Chromatography B, vol. 754, 2001, pp. 153-159.
Hidenao Toyoda et al., "Determination of human urinary hyaluronic acid, chondroitin sulphate and dermatan sulphate as their unsaturated disaccharides by high-performance liquid chromatography", Journal of Chromatography, vol. 565, 1991, pp. 141-148.
Written Opinion issued in PCT/US03/13517 (Oct. 28, 2004) (Parent application), Oct. 28, 2004.
Joseph Alroy, et al., "Application of lectin histochemistry and carbohydrate analysis to the characterization of lysosomal storage diseases", Carbohydrate Research, XP 002468988, vol. 213, Jun. 25, 1991, pp. 229-250.

(Continued)

*Primary Examiner* — Gary W Counts
(74) *Attorney, Agent, or Firm* — Oblon, Spivak, McClelland, Maier & Neustadt, L.L.P.

(57) ABSTRACT

A method for detecting lysosomal storage diseases including the steps of performing an assay for a single species of glycosaminoglycan contained in a specimen and correlating results of the assay with lysosomal storage diseases. A body fluid such as urine or blood can be employed as a specimen. The assay can be performed by use of a polypeptide that is capable of specifically binding to a glycosaminoglycan-containing molecule. The polypeptide may be an antibody, or a polypeptide having an antigen-binding site of an antibody.

19 Claims, 7 Drawing Sheets

(56) References Cited

OTHER PUBLICATIONS

Dembure, et al. Techniques in Diagnostic Human Biochemical Genetics, a Laboratory Manual, Screening for Mucopolysaccharidoses by Analysis of Urinary Glycosaminoglycans, 1991, pp. 77-86.

Sewell et al., Klin. Wochenschr. Comprehensive Urinary Screening for Inborn Errors of Complex Carbohydrate Metabolism, 57, 1979, 581-585.

Anatole S. Dekaban, et al. "Mucopolysaccharidoses, Relation of Elevated Cerebral Spinal Fluid to Mental Retardation", Arch Neurol, vol. 28, Jun. 1973, pp. 385-388.

Robert P. Erickson, et al., "Lack of Relationship Between Blood and Urine Levels of Glycosaminoglycans and Lysomal Enzymes", Biochemical Medicine, vol. 12, No. 4, 1975, pp. 331-339.

J, Melet, et al., "A Semi-Quantitative Micromethod for the Determination of Free Glycosaminoglycans in Serum. Results From Studies on Serum of Healthy Children of Various Age and Patients Affected by Mucopolysaccharidosis", Clinica Chimica Acta, vol. 108, No. 2, Dec. 8, 1980, pp. 179-188.

B, Marcri, et al., "Mucopolysaccharidosis VI in a Siamese/Short-Haired European Cat", Journal of Veterinary Medicine A.. vol. 49, No. 8, Oct. 2002, pp. 438-442.

Strongin, Sensitivity, Specificity and Predictive Value of Diagnostic Tests: Definitions and Clinical Applications, Laboratory Diagnosis of Viral Infections, $2^{nd}$ edition, 1992, pp. 211-219.

Tanaka et al., Detection of urinary keratan sulfate with the sue of monocional antibody, vol. 19 No. 3-4, pp. 236-237, Ketsugo Soschiki (1997).

Thuy, Le Phuc et al., A new quantitative assay for gglycosaminoglycans, Clinica Chimica Acta, vol. 212, pp. 17-26, 1992.

Bhavanandan et al., Quantitation of urinary glycosaminoglycans with Alcian blue: evaluation of the interference by Tamm-Horsfall glycoprotein, Clinica Chimica Acta 251 (196) 207-214).

Kongtawelert et al., A new ELISA methof for the determination of keratan sulphate peptides in biological fluids employing a monocional antibody and labelled avidin biotin technique, clinica Chimica acta, 195 (1990) 17-26.

PTO 02-4824 English Translation of Tanaka et al., Detection of urinary keratan sulfate with the use of monoclonal antibody. vol. 19, No. 3-4, pp. 236-237, Ketsugo Soshiki (1997).

Office Action issued Jun. 9, 2009, in Japanese Patent Application No. 2004-500786 (with English-language translation), Jun. 9, 2009.

Final Rejection issued May 29, 2012 in Japanese Patent Application No. 2009-206047 (with English translation), May 29, 2012.

Notification of Reasons for Refusal issued Jan. 31, 2012 in Japanese Patent Application No. 2009-206047, Jan. 31, 2012.

European Office Action dated Mar. 14, 2013 in corresponding European Patent Application No. 0372435537, 10 pp., Mar. 14, 2013.

Neufeld, EF, et al., "The mucopolysaccharidoses", The Metobolic and Molecular Bases of Inherited Disease, McGraw-Hill, vol. 4, 8th edition, Jan. 1, 2001, pp. 3421-3452.

Coppa G. V., et al., "Glycosaminoglycans from Urine and tissues in mucolipidosis II (I-cell disease)", Clinica Shimica Acta, Elsevier BV, Amsterdam, nl, vol. 95, No. 1, Jul. 2, 1979, pp. 135-137.

Tomatsu S., et al., "Herparan sulfat levels in mcopolysaccharidoses and mucolipidoses" Journal of Inherited Metobolic Disease, Kluwer Academic Publishers, Do, vol. 28, No. 5, Sep. 1, 2005, pp. 743-757.

Notification of Appeal issued Sep. 27, 2012 in Japanese Application No. 2009-206047 (With English Translation), Sep. 27, 2012.

Biochemistry Dictionary (third edition), Tokyo Kagaku Doujin Co., Ltd., Oct. 8, 1998, pp. 404, 1385 and 472 (With Partial English Translation), Oct. 8, 1998.

\* cited by examiner

METHOD FOR DETECTING LYSOSOMAL STORAGE DISEASES

This application is a continuation of U.S. application Ser. No. 10/512,839, filed May 10, 2005 (now U.S. Pat. No. 7,951, 545), which was a U.S. national-stage filing of PCT/US03/013517, filed Apr. 30, 2003, which claimed priority under 35 U.S.C. 119(e) to U.S. Provisional Application No. 60/441, 325, filed Jan. 22, 2003 and U.S. Provisional Application No. 60/376,194, filed Apr. 30, 2002.

TECHNICAL FIELD

The present invention relates to a method for detecting lysosomal storage diseases and to a kit therefor.

BACKGROUND ART

The following abbreviations are used throughout the present specification:
- GAG: glycosaminoglycan
- KS: keratan sulfate
- HS: heparan sulfate
- CS: chondroitin sulfate
- CS-4S: chondroitin-4-sulfate
- CS-6S: chondroitin-6-sulfate
- DS: dermatan sulfate (also called chondroitin sulfate B)
- GSD I: glycogen storage disease type 1
- GSD II: glycogen storage disease type 2 (Pompe disease)
- Hep: heparin
- HA: hyaluronic acid
- LIPO: lipofuscinoses
- MPS: mucopolysaochaxidoses
- ML: mucolipidoses
- MLD: metachromatic leukodystropy
- NP: Niemann-Pick diseases
- TS: Tay-Sachs disease Lysosomal storage diseases are diseases caused by abnormality of enzymes present in lysosomes.

Mucopolysaccharidoses are kinds of lysosomal storage diseases and form a class of hereditary diseases caused by deficiency of enzymes (lowered activity of enzymes) involved in degradation metabolism of GAGs. In accordance with the species of the defective enzyme, GAG of a specific species is known to be accumulated in tissues and excreted into body fluids. Clinical manifestations of mucopolysaccharidoses are diversified, but most cases involve coarse facial expression, dysostosis multiplex, and visceromegaly. In same oases, hypacusia, cardiovascular disorders, and mental retardation are also observed.

Table 1-1 shows the known relations between types of mucopolysaccharidoses and corresponding GAGs that are accumulated (see, for example, "The Metabolic and Molecular Bases of Inherited Disease", 7th edn., Scriver C R, Beaudet A L, Sly W S, Valle D (eds.), 1995, McGraw-Hill, New York).

TABLE 1-1

| | | mucopolysaccharidoses | |
|---|---|---|---|
| Type | Disease Name | Enzyme Deficiency | Substance Stored |
| I H | Hurler Syndrome | α-L-iduronidase | HS, DS |
| I S | Scheie Syndrome | same as above | HS, DS |

TABLE 1-1-continued

| | | mucopolysaccharidoses | |
|---|---|---|---|
| Type | Disease Name | Enzyme Deficiency | Substance Stored |
| I H/S | Hurler-Scheie Complex | same as above | HS, DS |
| II A | Hunter Syndrome (Severe) | iduronate sulfatase | HS, DS |
| II B | Hunter Syndrome (Mild) | same as above | HS, DS |
| III A | Sanfilippo Syndrome A | heparan N-sulfatase | HS |
| III B | Sanfilippo Syndrome B | α-N-acetylglucosaminidase | HS |
| III C | Sanfilippo Syndrome C | acetyl CoA: α-glucosaminide N-acetyltransferase | HS |
| III D | Sanfilippo Syndrome D | N-acetylglucosamine-6-sulfatase | HS |
| IV A | Morquio Syndrome A | galactosamine-6-sulfatase | KS |
| IV B | Morquio Syndrome B | β-galactosidase | KS |
| VI A | Maroteaux-Lamy Syndrome (Severe) | arylsulfatase B | DS |
| VI B | Maroteaux-Lamy Syndrome (Mild) | same as above | DS |
| VII | β-glucuronidase deficiency | β-glucuronidase | HS, DS, CS-4S, CS-6S |

TABLE 1-2

| | | mucolipidoses | |
|---|---|---|---|
| Type | Disease Name | Enzyme Deficiency | Substance Stored |
| II | I-Cell disease | N-acetylglucosamine-1-phosphotransferase | Inclusion body |
| III | Pseudo-Hurier Polydystrophy | same as above (Mild) | Inclusion body |

However, until the present invention, it has remained unknown that each case of the mentioned mucopolysaccharidoses not only involves excretion in body fluids of the GAG species shown in Table 1-1, but also involves excretion in body fluids of large amounts of other species of GAGs.

Japanese Patent Application Laid-Open (kokai) No. 10-153600 discloses an assay method in which a solid phase to which a first receptor (anti-GAG antibodies such as anti-KS antibody, anti-CS antibody, anti-HS antibody or the like) is immobilized is brought into contact with a specimen containing a first ligand (GAG such as KS, CS, HS or the like), and formation of a complex between the first receptor and the first ligand is detected by a first-labeling-substance-labeled first receptor, to thereby assay the first ligand contained in the specimen. This publication also discloses that the method facilitates primary screening of GAG-related diseases (including mucopolysaccharidoses such as Morquio's syndrome and Hurler's syndrome).

However, Japanese Patent Application Laid-Open (kokai) No. 10-153600 neither discloses nor suggests that each case of the aforementioned mucopolysaccharidoses involves, in addition to the GAG species shown in Table 1-1 being excreted, excretion into body fluid of large amounts of other species of GAGs. Moreover, this publication neither discloses nor suggests whether measurement of GAG of a single species enables detection of all types of mucopolysaccharidoses, regardless of the classification (type) of mucopolysaccharidoses.

Mucolipidoses are also kinds of lysosomal storage diseases and are diseases that show similar clinical symptoms to those of mucopolysaccharidoses. It is known that types of the mucolipidoses are as shown in Table 1-2.

Also, GM1 gangliosidoses and fucosidoses are also kinds of lysosomal storage diseases. GM1 gangliosidoses are diseases in which GM1 ganglioside and β-galactose residue-containing oligosaccharides and glycoproteins are accumulated due to impediment in β-galactosidase, and fucosidoses are diseases in which oligosaccharides and glycoproteins having α-fucose residues are accumulated due to impediment in α-fucosidase.

In addition, galactosialidoses are also kinds of lysosomal storage diseases and are diseases in which sialyloligosaccharides and substances similar to the case of GM1 gangliosidoses are accumulated due to impediment in β-galactosidase and α-neuraminidase, and impediment in cathepsin A which is involved in the stabilization of these enzymes.

Furthermore, the following diseases are also kinds of lysosomal storage diseases.

Metachromatic leukodystrophy is a disease in which sulphatides are accumulated due to impediment in arylsulfatase A.

Niemann-Pick diseases are diseases in which sphingomyelin is accumulated. Niemann-Pick type B is due to impediment in acid sphingomyelinase, and Niemann-Pick type C is due to cholesterol esterification defect.

Tay-Sachs disease is disease in which GM2 ganglioside is accumulated due to impediment in α-subunit of N-acetyl-β-D-glucosaminidase A.

Sandhoff disease is disease in which GM2 ganglioside is accumulated due to impediment in β-subunit of N-acetyl-β-D-glucosaminidase A and B.

GM2 gangliosidoses are diseases in which GM2 ganglioside is accumulated due to impediment in GM2 activator protein.

Krabbe disease is disease in which galactocerebroside is accumulated due to impediment in β-D-galactocerebrosidase.

Fabry disease is disease in which globosides are accumulated due to impediment in α-D-galactosidase.

Gaucher diseases are diseases in which glucosylceramide is accumulated due to impediment in β-D-glucocerebrosidase.

Glycogen storage disease type 1 is disease in which glycogen is accumulated due to impediment in glucose-6-phosphatase.

Glycogen storage disease type 2 (also called Pompe disease) is disease in which glycogen is accumulated due to impediment in α-D-glucosidase.

Lipofuscinoses are caused by impediment in palmitoyl-protein thioesterase or tripeptidyl amino peptidase-I.

It has not been known that GAG is also discharged in a large amount into body fluids in these diseases.

Hereinafter, mucopolysaccharidoses, mucolipidoses, GM1 gangliosidoses, fucosidoses, galactosialidoses, metachromatic_leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses are referred to as "mucopolysaccharidoses, etc."

In general, mucopolysaccharidoses, etc. are asymptomatic in newborns, but onset thereof becomes clear by manifestations including arrested height gain, abnormal development of bones, and growth of shaggy hair during infancy or childhood. In some cases, although subjects are normal during neonatal periods, mental retardation gradually progresses over years. Therefore, diagnosis of mucopolysaccharidoses, etc. in an early newborn stage during which no clinical syndromes are manifested may possibly prevent mental retardation, etc., through early enzyme replacement therapy, genetic treatment, or bone marrow transplantation. Therefore, diagnosis of mucopolysaccharidoses, etc. is desirably performed for all newborns.

However, in Japan, for example, the number of newborns per year exceeds 1,000,000, and the frequency of onset of mucopolysaccharidoses, etc. is as low as one per 40,000 to 50,000, and since current diagnosis therefor, which detects deficiency or abnormality of enzymes, is cumbersome and expensive, demand exists for an accurate screening method to be performed before such an expensive diagnosis. In other words, if there can be provided a method for detecting patients suffering mucopolysaccharidoses, etc. with high accuracy, with high sensitivity, conveniently, quickly, and at low cost, without overlooking any patients of mucopolysaccharidoses, etc., presence or absence of mucopolysaccharidoses, etc. can be detected in all newborns, and thus precise, definite diagnosis of every patient of mucopolysaccharidoses, etc. can be attained at an early stage of the disease.

DISCLOSURE OF THE INVENTION

Accordingly, an object of the present invention is to provide a very accurate, sensitive method for detecting lysosomal storage diseases which can be performed conveniently, quickly, and at low cost. Another object of the invention is to provide a kit for detecting lysosomal storage diseases.

The present inventors have carried out extensive research in an attempt to attain the above objects, and have found the following: in spite of conventional understanding that, in accordance with the type (classification) of mucopolysaccharidosis, only GAG of a specific species is excreted into body fluids in large amounts, in reality other species of GAGs are also excreted abundantly. Moreover, the present inventors found that GAG is also excreted into body fluids in large amounts in mucopolysaccharidoses, mucolipidoses, GM1 gangliosidoses, fucosidoses, galactosialidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses. On the basis of this finding, the inventors have achieved a highly accurate, highly sensitive, convenient, effective, inexpensive method and kit for detecting lysosomal storage diseases, thus leading to completion of the invention.

Accordingly, the present invention provides a method for detecting lysosomal storage diseases, comprising the steps of performing an assay for GAG of a single species contained in a specimen, and correlating results of the assay with lysosomal storage diseases (hereinafter the method is called "the method of the invention" or "the present method").

Preferably, the "lysosomal storage diseases" are at least one disease selected from mucopolysaccharidoses, mucolipidoses, GM1 gangliosidoses, fucosidoses, galactosialidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses.

Preferably, the specimen is a body fluid, with urine or blood being more preferred.

Preferably, the assay of the mentioned single species of GAG is performed by use of a polypeptide that is capable of specifically binding to a GAG-containing molecule.

Preferably, the assay comprises the following steps (1) and (2):

(1) a step for forming a sandwich-like complex by bringing "a solid phase to which a first polypeptide capable of specifically binding to a GAG-containing molecule is immobilized", "a specimen", and "a second polypeptide capable of specifically binding to a GAG-containing molecule" into contact with one another, the sandwich-like complex being constituted by "said first polypeptide immobilized onto the solid phase—GAG-containing molecule in the specimen—second polypeptide"; and (2) a step for detecting the sandwich-like complex formed in step (1).

More preferably, the assay comprises the following steps (1), (2), and (3):

(1) a step for forming a complex by bringing "a solid phase to which a first polypeptide capable of specifically binding to a GAG-containing molecule is immobilized" into contact with "a specimen", the complex being constituted by "first polypeptide immobilized onto the solid phase—GAG-containing molecule in the specimen";

(2) a step for forming a sandwich-like complex by bringing the above-described solid phase into contact with "a second polypeptide capable of specifically binding to a GAG-containing molecule", the sandwich-like complex being constituted by "said first polypeptide immobilized onto the solid phase—GAG-containing molecule in the specimen—second polypeptide"; and (3) a step for detecting the sandwich-like complex formed in step (2).

Preferably, the "second polypeptide" is labeled with a labeling substance or, alternatively, is capable of being labeled with a labeling substance.

Preferably, the assay comprises the following steps (1) and (2):

(1) a step for forming first and second complexes by bringing "a third polypeptide capable of specifically binding to a GAG-containing molecule", "a specimen", and "a solid phase to which a GAG-containing molecule is immobilized" into contact with one another, the first complex being constituted by "GAG-containing molecule immobilized onto a solid phase—third polypeptide" and the second complex being constituted by "GAG-containing molecule is the specimen—third polypeptide"; and (2) a step for detecting at least one of the complexes formed in step (1), the first complex being "GAG-containing molecule immobilized onto a solid phase—third polypeptide" and the second complex being "GAG-containing molecule in the specimen—third polypeptide."

More preferably, the assay comprises the following steps (1) to (3):

(1) a step for forming a first complex by bringing into contact "a third polypeptide capable of specifically binding to a GAG-containing molecule" and "a specimen", the first complex being constituted by "third polypeptide—GAG-containing molecule in the specimen";

(2) a step for forming a second complex by bringing "the solid phase to which a GAG-containing molecule is immobilised" into contact with a mixture resulting from step (1) which contains "the first complex" and "a third polypeptide that participated in formation of the first complex", the second complex being constituted by "GAG-containing molecule immobilized onto the solid phase—third polypeptide"; and (3) a step for detecting the second complex formed in step (2).

Detection of the second complex is preferably carried out by use of a fourth polypeptide capable of being specifically binding to the third polypeptide and having been labeled with, or being capable of being labeled with, a labeling substance.

Any of the polypeptides employed in the above methods is preferably an antibody or a polypeptide having an antigen-binding site of an antibody.

In the method of the present invention, preferably, the "GAG of a single species" is a GAG having a sulfate group. The GAG having a sulfate group is preferably KS, HS, CS, or DS. In the present method, preferred are the cases where the "GAG having a sulfate group" is KS, and simultaneously, the "mucopolysaccharidoses" are of one or more types selected from among mucopolysaccharidosis types I, II, III, VI, and VII. Also preferred are the cases where the "GAG having a sulfate group" is KS, and the mucolipidoses are of one or more types selected from among mucolipidosis types II and Also preferred are the cases where the "GAG having a sulfate group" is HS, and simultaneously, the "mucopolysaccharidoses" are of one or more types selected from among mucopolysaccharidosis types IV and VI; the cases where the "GAG having a sulfate group" is HS, and the lysosomal storage diseases are of one or more diseases selected from among mucolipidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses; the cases where the "GAG having a sulfate group" is CS, and simultaneously, the "mucopolysaccharidoses" are of one or more types selected from among mucopolysaccharidosis types I, II, III, IV, and VI; and the cases where the "GAG having a sulfate group" is DS, and simultaneously, the "mucopolysaccharidoses" are of one or more types selected from among mucopolysaccharidosis types III and IV.

The present invention also provides a kit for detecting at least one disease selected from mucopolysaccharidoses, mucolipidoses, GM1 gangliosidoses, fucosidoses, galactosialidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses comprising the following components and used for detecting at least one disease selected from mucopolysaccharidoses, mucolipidoses, GM1 gangliosidoses, fucosidoses, galactosialidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses on the basis of assay results of GAG of a single species contained in a specimen (hereinafter the kit is called "the kit of the invention" or "the present kit"):

(A) a solid phase to which a first polypeptide capable of specifically binding to a GAG-containing molecule is immobilized; and (B) a second polypeptide capable of specifically binding to a GAG-containing molecule and having been labeled with, or being capable of being labeled with, a labeling substance.

Alternatively, the kit of the present invention may comprise the following components:

(A) a solid phase to which a GAG-containing molecule is immobilized;

(B) a third polypeptide capable of specifically binding to a GAG-containing molecule; and (C) a fourth polypeptide capable of specifically binding to the third polypeptide, and having been labeled with, or being capable of being labeled with, a labeling substance.

Preferably, any of these polypeptides is an antibody or a polypeptide having an antigen-binding site of an antibody.

In the kit of the present invention, preferably, the "GAG of a single species" is a GAG having a sulfate group. The GAG having a sulfate group is preferably KS, HS, CS, or DS. In the present kit, preferred are the cases where the "GAG having a sulfate group" is KS, and simultaneously, the "mucopolysaccharidoses" are of one or more types selected from among mucopolysaccharidosis types I, II, III, VI, and VII. Also preferred are the cases where the "GAG having a sulfate group" is KS, and the mucolipidoses are of one or more types selected from among mucolipidosis types II and III. Also preferred are the cases where the "GAG having a sulfate group" is HS, and simultaneously, the "mucopolysaccharidoses" are of one or more types selected from among mucopolysaccharidosis types IV and VI; the cases where the "GAG having a sulfate group" is HS, and the diseases are of one or more diseases selected from among mucolipidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses; the cases where the "GAG having a sulfate group" is CS, and simultaneously, the "mucopolysaccharidoses" are of one or more types selected from among mucopolysaccharidosis types I, II, III, IV, and VI; and the cases where the "GAG having a sulfate group" is DS, and simultaneously, the "mucopolysaccharidoses" are of one or more types selected from among mucopolysaccharidosis types III and IV.

Various modes of the present invention will next be described.

<1> Method of the Present Invention

The present invention contemplates a detection method for lysosomal storage diseases, and comprises the steps of measuring GAG of a single species contained in a specimen and correlating the measurement results with lysosomal storage diseases.

Preferably, the present invention contemplates a detection method for at least one disease selected from mucopolysaccharidoses, mucolipidoses, GM1 gangliosidoses, fucosidoses, galactosialidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses and comprises the steps of measuring GAG of a single species contained in a specimen and correlating the measurement results with at least one disease selected from mucopolysaccharidoses, mucolipidoses, GM1 gangliosidoses, fucosidoses, galactosialidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses.

A characteristic feature of the method of the present invention resides in the detection of mucopolysaccharidoses through measurement of GAG of "a single species", rather than through measurement of GAG of "a plurality of species" contained in a specimen. It has hitherto been accepted that depending on the classification (type) of mucopolysaccharidoses, different species of GAGs are accumulated and excreted. Therefore, quite naturally, according to conventional understanding, even when the measurement of a certain species of GAG (e.g., KS) is negative, presence of mucopolysaccharidoses cannot be denied until measurements of other species of GAG (e.g., HS, CS, DS or the like) support the negative results. That is, conventionally, in order to detect mucopolysaccharidoses, a plurality of species of GAGs must be measured for a single specimen.

In contrast, the method of the present invention enables correlation with mucopolysaccharidoses to be established by the measurement of only GAG of a single species. Furthermore, the method of the present invention enables correlation with not only mucopolysaccharidoses but also at least one disease selected from mucolipidoses, GM1 gangliosidoses, fucosidoses, galactosialidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses.

Although no particular limitation is imposed on the specimen that can be used in the present invention, body fluid is preferred. No particular limitation is imposed on the body fluid, so long as it contains, or possibly contains, GAG accumulated as a result of lysosomal storage diseases. Examples of the body fluid include urine, blood (as used herein, the term "blood" is used to encompasses serum and plasma), saliva, sweat, tears, synovial fluid, cartilage extracts, and supernatants of cell cultures. Of these, urine and blood are preferred, as they are easily collected from newborns and in fact are routinely collected for usual newborn health check items.

When blood is used as the body fluid, the collected blood sample may be used as is without any treatment, or serum or plasma derived from the collected blood sample may be used. Preferably, serum or plasma is employed. Alternatively, hydrophilic components may be extracted from the blood sample, after which GAG contained in the extract is measured. No particular limitation is imposed on the method For extracting hydrophilic components; for example, a droplet of a blood sample is added onto commercial filter paper, and hydrophilic components are extracted from the filter paper. Extraction of the hydrophilic components from the filter paper may be Conveniently performed by soaking, in an aqueous solution, the filter paper bearing the droplet of the blood sample.

No particular limitation is imposed on the subjects from which body fluids are collected, so long as they are individuals having chances of suffering from lysosomal storage diseases. Preferably, such individuals are mammals, and more preferably the mammals are humans. In particular, humans ranging in age from just-delivered newborns to about 6-month infants are preferred.

The "GAG of a single species" to be used in the method of the present invention should be understood in its literal meaning; i.e., one species of GAG. There may be cases where such a single species of GAG is linked with other components to thereby form a complex, and in such cases, the expression "GAG of a single species" is used to mean that a single species of GAG is present in the complex. For example, when GAG is bound to a protein and forms proteoglycan, "GAG of a single species" refers to the case where a single species of GAG is present in the proteoglycan.

Examples of "GAG" include KS, HS, CS, DS (which is sometimes called chondroitin sulfate B), Hep, and HA. Preferably, GAG has a sulfate group. In particular, GAG is preferably KS, HS, CS, or DS, more preferably KS or HS, most preferably KS.

Examples of "proteoglycan" formed up of GAG and protein attached thereto include, but are not limited to, decorin (DS is attached to the core protein), aggrecan (CS and KS are attached to the core protein), versican (DS is attached to the core protein), keratocan (KS is attached to the core protein), syndecan (CS and HS are attached to the core protein), and perlecan (HS is attached to the core protein).

No particular limitation is imposed on the method for the "measurement" of any single species of these GAGs contained in a specimen, so long as the method enables detection of the single species of GAG. As used herein, the word "measurement" (or "assay") encompasses not only quantitative detection of GAG but also qualitative detection (i.e., detection of presence or absence of GAG).

Measurement of GAG of a single species (or in other words, measurement of a certain GAG species) may be performed through any of the following methods:

i) a method employing a polypeptide capable of specifically binding to the GAG;

ii) a method for analysis using various chromatography. The method using chromatography is not particularly limited, and includes various chromatography methods such as a gas chromatography method and a liquid chromatography. Examples include a method in which a degradation enzyme capable of specifically reacting with a certain species of GAG is caused to react with the GAG contained in a specimen, to thereby obtain a degradation product (disaccharide), and through high performance liquid chromatography (HPLC) the elution time of the product from the ion exchange column is analyzed (disaccharide analysis);

iii) a method in which a degradation enzyme capable of specifically reacting with a certain species of GAG is caused to react with the GAG contained in a specimen, and the presence or absence, as well as the degree, of degradation of the GAG is determined by use of a dye capable of reacting with the GAG;

iv) a method in which a degradation enzyme capable of specifically reacting with a certain species of GAG is caused to react with the GAG contained in a specimen, and the presence or absence, as well as the degree, of degradation of the GAG is determined by use of a polypeptide capable of specifically binding to the GAG. The method iv) is also described hereinbelow in Example 1; and v) a method for analysis using a mass spectrometry. The method using a mass spectrometer is not particularly limited, and includes various mass spectrometry methods such as a tandem mass spectrometry method (MS/MS) and a MALDI/TOFMS method.

Of these methods, those employing a polypeptide capable of specifically binding to GAG are preferred.

Preferably, the "polypeptide" is an antibody or a polypeptide having an antigen-binding site (Fab) of an antibody. The "polypeptide having an Fab of an antibody" may be a fragment containing an Fab of an antibody. The Fab-containing fragment may be produced by treating an antibody with a protease (such as plasmin, pepsin, papain or the like) that does not degrade Fab. Examples of the Fab-containing fragment also include Fabc, (Fab')$_2$ and the like, in addition to Fab.

The "polypeptide having an Fab of an antibody" may be a chimera antibody having an Fab of interest. When the nucleotide sequence of a gene coding for the antibody or the amino acid sequence of the antibody is determined, there can be genetically produced a chimera antibody having an Fab of interest or a fragment containing an Fab of interest.

The "polypeptide" is preferably purified in advance. When the polypeptide is an "antibody" and the immunoglobulin class thereof is IgG, the polypeptide can be purified by means of affinity chromatography making use of protein A or Protein G. When the immunoglobulin class of an antibody is IgM, the polypeptide is purified by means of gel filtration column chromatography.

No particular limitation is imposed on the "antibody" employed in the present invention, so long as it is capable of specifically binding to a GAG of a single species and either of monoclonal antibodies and polyclonal antibodies may be used. From the viewpoints of specificity, homogeneity, reproducibility, and productivity in sustainable abundance, monoclonal antibodies are preferred.

The "antibody" may be produced by a known method (for example, for anti-KS antibody, see *J. Biol. Chem.*, 258, 8848-8854 (1983); and for anti-CS antibody, see *J. Biol. Chem.*, 262, 4146-4152 (1987)). Alternatively, the "antibody" may be produced by following either of the below-described general methods.

1) Method for Producing a Polyclonal Antibody

An antigen is administered to animals for immunization, such as mice, rats, guinea pigs, rabbits, goat, sheep, horses, pigs, dogs, cats, or chickens under the skin (subcutaneously), into the abdominal cavity (intraperitoneally), or in a footpad.

Use of an adjuvant during immunization of animals is preferred, since adjuvants activate antibody-producing cells. When the animals receive boosters in a usual manner two to three weeks following the initial immunization, antisera of high titer can be obtained. About one week following the final immunization, blood is collected and serum is separated. The serum is treated with heat to thereby deactivate complements. Immunoglobulin fractions may be purified through a conventional purification method employed for antibodies.

2) Method for Producing a Monoclonal Antibody

A monoclonal antibody may be prepared by the method of Kohler and Milstein (*Nature*, 256, 495-497 (1975)).

For example, an antigen is administered to animals for immunization, such as mice, rats, guinea pigs, rabbits, goat, sheep, horses, pigs, dogs, cats, or chickens intraperitoneally, subcutaneously, or in a footpad.

From the immunized animals, spleen cells, lymphocytes, peripheral blood, etc. are collected, and subjected to cell fusion with myeloma cells (which are of tumor cell line), to thereby prepare hybridomas. The myeloma cells to be used in cell fusion may be obtained from various cell lines of mammals. Preferably, cell lines from animals of the same species as the immunized animals are employed. Also preferably, the myeloma cells bear a marker for discernment, after cell fusion, between unfused cells and fused cells, to thereby enable growth of only hybridomas, while preventing survival of unfused myeloma cells. Also, in order to facilitate collection of antibodies of interest from a culture supernatant of hybridoma, the myeloma cells are preferably of a cell line which does not secrete inherent immunoglobulins.

The obtained hybridomas are continuously grown, and subsequently, hybridoma cell lines which continuously produce antibodies capable of specifically binding to antigens are selected through screening.

The thus-selected hybridoma cell line is cultured by use of a suitable medium, to thereby obtain monoclonal antibodies in the medium. It is also possible to mass-produce monoclonal antibodies by culturing said hybridoma cell line in a living body; e.g., in the abdominal cavity of a mouse, and then separating the hybridoma cell line from the ascites. The thus-obtained monoclonal antibodies may be purified through a conventional purification method employed for antibodies.

Although no particular limitation is imposed on the immunoglobulin class of the antibodies, IgG is preferred. Antibodies whose immunoglobulin class is IgG can be obtained through screening by use of an anti-IgG antibody.

The definition of "GAG of a single species" has already been provided hereinabove. Thus, the "polypeptide capable of specifically binding to GAG" is preferably a polypeptide capable of specifically binding to a GAG having a sulfate group; more preferably a polypeptide capable of specifically binding to KS, HS, CS, or DS; even more preferably a polypeptide capable of specifically binding to KS or HS; most preferably a polypeptide capable of specifically binding to KS.

The "polypeptide capable of specifically binding to GAG" may be, but is not limited to, the commercial products described below. The descriptions in parentheses indicate animals from which the immunoglobulins are obtained and the immunoglobulin classes.

Polypeptide Capable of Specifically Binding to KS:

Anti-KS antibody "5D4" (mouse, IgG1). "5D4" is a monoclonal antibody which specifically binds to KS.

Polypeptide Capable of Specifically Binding to HS:

Anti-HS antibodies "HepSS-1" (mouse, IgM), "F58-10E4" (mouse, IgM), "HK-249" (mouse, IgM), "F69-3G10" (mouse, IgG2b), "JM403" (mouse, IgM (*Diabetologia*, 37(3), 313-320 (1994))). These are all monoclonal antibodies which specifically bind to HS.

Polypeptide Capable of Specifically Binding to DS and CS:

Anti-CS antibodies "CS-56" (mouse, IgM), "MO-225" (mouse, IgM), "MC21C" (mouse, IgM), "LY111" (mouse, IgM), "1-B-5" (mouse, IgG1), "2-B-6" (mouse, IgG1), "3-B-3" (mouse, IgM), "2H6" (mouse, IgM), and "473" (mouse, IgA). These are all monoclonal antibodies which specifically bind to HS.

The above antibodies are already known and, except for JM403, are commercially available from Seikagaku Corporation (Tokyo). Therefore, persona having ordinary skill in the art can prepare or procure them without difficulty.

Example assay methods for "GAG of a single species" by use of a polypeptide capable of specifically binding to GAG include, but are not limited to, the following.

i) A specimen is brought into contact with a solid phase to which a first polypeptide is immobilized, followed by addition of a second polypeptide for contact thereto, to thereby form a sandwich-like complex, and the thus-formed complex is detected (a so-called sandwich assay).

ii) In the presence of three components; that is, GAG-containing molecules which is immobilized onto a solid phase, a specimen, and a polypeptide (wherein the specimen and the polypeptide may be brought into contact in advance), the GAG-containing molecules which is immobilized and GAG-containing molecules contained in the specimen are allowed to competitively react with the polypeptide, and subsequently, the amount of polypeptide bound to the solid phase is detected, to thereby obtain the amount of GAG contained in the specimen (a so-called inhibition assay).

iii) A specimen is brought into contact with fine particles to which polypeptide molecules is immobilized, followed by addition of a second polypeptide for contact thereto, to thereby form aggregates of particles, and the thus-formed aggregates (or precipitates) are detected (a so-called agglutination assay).

Preferably, the present method is carried out through a sandwich assay. That is, the present method preferably comprises the following steps:

(1) a step for forming a sandwich-like complex by bringing "a solid phase to which a first polypeptide capable of specifically binding to a GAG-containing molecule is immobilized", "a specimen", and "a second polypeptide capable of specifically binding to a GAG-containing molecule" into contact with one another, the sandwich-like complex being constituted by "said first polypeptide immobilized onto the solid phase—GAG-containing molecule in the specimen—second polypeptide"; and (2) a step for detecting the sandwich-like complex formed in step (1).

In step (1) above, the three substances; i.e., "a solid phase to which a first polypeptide capable of specifically binding to a GAG-containing molecule is immobilized", "a specimen", and "a second polypeptide capable of specifically binding to a GAG-containing molecule" may be brought into contact simultaneously. Alternatively, the former two substances may first be brought into contact with each other, followed by addition of the third substance for contact; or the latter two substances may first be brought into contact with each other, followed by addition of the first substance for contact. Preferably, according to the method of the present invention, the former two substances are first brought into contact with each other, followed by addition of the third substance for contact. Thus, more preferably, the assay comprises the following steps (1), (2), and (3):

(1) a step for forming a complex by bringing "a solid phase to which a first polypeptide capable of specifically binding to a GAG-containing molecule is immobilized" into contact with "a specimen", the complex being constituted by "first polypeptide immobilised onto the solid phase—GAG-containing molecule in the specimen";

(2) a step for forming a sandwich-like complex by bringing the above-described solid phase into contact with "a second polypeptide capable of specifically binding to a GAG-containing molecule", the sandwich-like complex being constituted by "said first polypeptide immobilized onto the solid phase—GAG-containing molecule in the specimen—second polypeptide"; and (3) a step for detecting the sandwich-like complex formed in step (2).

Hereafter, this method will be explained in detail for every process.

Step (1):

In step (1), "a solid phase to which a first polypeptide capable of specifically binding to a GAG-containing molecule is immobilized" is brought into contact with "a specimen", to thereby form a complex constituted by "first polypeptide immobilized onto the solid phase—GAG-containing molecule in the specimen."

(1)-1 First Polypeptide Capable of Specifically Binding to a GAG-Containing Molecule As used herein, the term "GAG-containing molecule" refers to any molecule that contains GAG as a constituent thereof. Examples of such a molecule include a GAG molecule per se (i.e., containing no other constituents), and a proteoglycan molecule.

The "first polypeptide" in this context may be the same as or different from the below-described "second polypeptide." However, in any case, at least one of the two must be a polypeptide capable of specifically binding to GAG (i.e., a GAG molecule per se).

The definition of "polypeptide capable of specifically binding to GAG (i.e., a GAG molecule per se)" has already been provided hereinabove. An example of a "polypeptide capable of specifically binding to a GAG-containing molecule (other than the GAG molecule per se)" is an antibody capable of specifically binding to the core protein of proteoglycan. Examples of such an antibody include, but are not limited to, "6-B-6" (mouse, IgG1) (anti-decorin antibody), "2-B-1" (mouse, IgG1) (anti-versican antibody), "HK-102" (mouse, IgG2b) (anti-perlecan antibody), "1-G-2" (mouse, IgG1) (anti-neurocan antibody), and "6-B-4" (mouse, IgM) (anti-phosphacan antibody). In the above description, the animals from which the immunoglobulins are derived and immunoglobulin classes are provided in parentheses.

The above are all monoclonal antibodies which are capable of binding to the core protein of proteoglycans. These antibodies are commercially available from Seikagaku Corporation (Tokyo).

When blood is used as a specimen, GAGs contained in the blood specimen are considered to be present in the form of proteoglycans. Therefore, the aforementioned "polypeptide capable of specifically binding to a GAG-containing molecule (other than the GAG molecule per se)" may be employed to serve as either one of the first polypeptide and a second polypeptide, which will be described hereinbelow. In this case, however, the other polypeptide must be a "polypeptide capable of specifically binding to GAG (i.e., a GAG molecule per se)."

(1)-2 Solid Phase

No particular limitation is imposed on the solid phase to which the first polypeptide is to be immobilised, so long as the solid phase is capable of immobilising the polypeptide and is insoluble in water, specimen, or reaction mixture of the assay. The solid phase may take a variety of forms, such as plates (e.g., wells of microplates), tubes, beads, membranes, gels, and micro-spherical solid carriers (gelatin particles, kaolin particles, or synthetic polymer particles such as latex). From the viewpoints of accurate quantitative evaluation and convenience in use, microplates are preferred.

Examples of the material that constitutes the solid phase include polystyrene, polypropylene, poly(vinyl chloride), nitrocellulose, Nylon, polyacrylamide, Teflon, polyallomer, polyethylene, glass, and agarose. Among these materials, polystyrene is preferred, and thus, plates made of polystyrene are preferred.

In order to immobilize the first polypeptide onto any of these solid phases, a conventional method for preparing immobilized enzymes may be applied, and such a method includes, for example, physical adsorption, covalent bonding, or entrapment ("Immobilized Enzymes" published by Kodansha, 1975, pp. 9-75).

In particular, physical adsorption is preferred from the viewpoints of convenience in procedure and prevalence in use.

A specific example of physical adsorption is described below. This example is drawn to a case where the first polypeptide is anti-KS antibody.

Anti-KS antibodies are dissolved in a buffer (e.g., phosphate buffer, phosphate buffered saline (PBS), or carbonate buffer; pH 7 to 9), and the solution is added onto a solid phase (such as a microplate), followed by storage for 1 to 2 hours at about 37° C. or overnight at about 4° C., to thereby immobilise the antibodies.

The surface of the solid phase to which the first polypeptide is immobilised may have portions bearing no peptide, and when GAG-containing molecules contained in the specimen adhere in an non-specific manner, accurate assay results may fail to be obtained. To prevent this, preferably, a blocking substance is added before the specimen is brought into contact with the solid phase, so as to cover the portions to which the first polypeptide has not yet been immobilized. Examples of such a blocking substance include serum albumin, casein, skim milk, gelatin, and Pluronic, and commercial products sold as such may also be employed.

In an exemplary blocking procedure, a blocking substance is added, followed by standing for 30 minutes to 2 hours at 37° C. or for 1 to 2 hours at room temperature (15-25° C.).

(1)-3 Specimen

Relevant descriptions provided hereinabove apply, and therefore repetition is omitted.

(1)-4 Contact Between Solid Phase and Specimen

No particular limitation is imposed on the manner in which the solid phase is brought into contact with the specimen, so long as the first polypeptide molecules immobilized onto the solid phase and the GAG-containing molecules contained in the specimen are under conditions allowing contact therebetween. For example, the specimen may be added onto the solid phase, or vice versa, for achieving contact therebetween. Alternatively, the two may be simultaneously added into a container which is provided separately. These are only examples, and contact between solid phase and specimen may be appropriately determined by persons having ordinary skill in the art in accordance with the shape, material, etc. of the solid phase.

When contact between the two has been established, preferably, the first polypeptide and GAG-containing molecules contained in the specimen are allowed to react at 4 to 37° C., more preferably at 37° C., for about 1 hour, so as to attain sufficient, complete bonding therebetween.

After completion of the above reaction, solid and liquid phases are separated from each other. Preferably, non-specific adsorbents or unreacted components remaining in the specimen are removed by washing the surface of the solid phase with a washing solution as desired.

Examples of preferred washing solutions include buffers to which nonionic surfactants (such as those of the Tween series) are incorporated, and specifically, mention may be given of phosphate buffer, PBS, and Tris HCl buffer.

When the specimen is brought into contact with the solid phase to which the first polypeptide is immobilized, a complex of "first polypeptide immobilized onto the solid phase—GAG-containing molecule" is formed.

Step (2):

In step (2), a second polypeptide capable of specifically binding to a GAG-containing molecule is brought into contact with the above-described solid phase that has undergone step (1), to thereby form a sandwich-like complex of "the first polypeptide immobilised onto the solid phase—GAG-containing molecule in the specimen—second polypeptide."

(2)-1 Second Polypeptide Capable of Specifically Binding to a GAG-Containing Molecule The descriptions provided hereinabove for the aforementioned "first polypeptide" also apply to the second polypeptide.

Preferably, the second polypeptide is labeled with, or can be labeled with, a labeling substance, so as to facilitate detection thereof. No particular limitation is imposed on the labeling substance which may be employed for labeling, so long as it can be ordinarily used for labeling proteins. Examples of such labeling substance include enzymes (such as peroxidase, alkaline phosphatase, β-galactosidase, luciferase, acetylcholinesterase, and glucose oxidase), radioisotopes (such as $^{125}$I, $^{131}$I, and $^{3}$H); fluorochromes (such as fluorescein isothiocyanate (FITC), 7-amino-4-methylcoumarin-3-acetate (AMCA), dichlorotriazinyl aminofluorescein (DTAF), tetramethylrhodamine isothiocyanate (TRITC), Lissamine Rhodamine B, Texas Red, Phycoerythrin (PE), umbelliferone, europium, phycocyanin, Tricolor, and crania); chemiluminescence substances (such as luminol); haptens (such as dinitrofluorobenzene, adenosine monophosphate (AMP), and 2,4-dinitroaniline); one component of any of specific binding pairs (such as biotin and an avidin (e.g., streptavidin), lectin and sugar chain, agonist and receptor therefor, heparin and antithrombin III (ATIII), and polysaccharide and a binding protein therefor (e.g., hyaluronic acid and hyaluronic-acid-binding protein (HABP)).

Of such exemplified labeling substances, one component of any of specific binding pairs is preferred, with either biotin or an avidin being more preferred. In particular, biotin is preferred.

The method for labeling the second polypeptide with a labeling substance may be performed through any known method suited for the substance of interest. For example, when the labeling substance is an enzyme, any of the following methods may be appropriately employed: glutaraldehyde method, periodate cross-linking method, maleimide cross-linking method, carbodiimide method, and activated ester method. When the labeling substance is a radioisotope, the chloramine T method or the lactoperoxidase method (see *Zoku-Seikagaku Jikken Koza* 2 "Protein Chemistry (the last volume)" published by Tokyo Kagaku Dojin, 1987) may be appropriately employed. For example, when biotin is employed as a labeling substance, there may be used a method in which an N-hydroxysuccinimide ester derivative or hydrazide derivative of biotin (see *Avidin-Biotin Chemistry: A Handbook*, PP. 57-63, Pierce Chemical Company, published in 1994).

Preferably, the second polypeptide is labeled with a labeling substance in advance.

(2)-2 Contact Between Solid Phase that has Undergone Step (1) and Second Polypeptide This step may be performed in a manner similar to that described in (1)-4 above. Also, similar to the case of step (1)-4, after completion of reaction, solid and liquid phases are separated from each other, and preferably, in accordance with needs, non-specific adsorbents and the unreacted components remaining in the specimen are removed through washing of the surface of the solid phase. Moreover, employable washing solutions are the same as described in connection with step (1)-4.

When the aforementioned solid phase that has undergone step (1) (i.e., the solid phase bearing a complex of "first polypeptide immobilized onto the solid phase—GAG-containing molecule in the specimen") is brought into contact with the second polypeptide capable of specifically binding to a GAG-containing molecule, a sandwich-like complex of "the first polypeptide immobilized onto the solid phase—GAG-containing molecule in the specimen—second polypeptide" is formed.

Step (3):

In step (3), the sandwich-like complex formed in step (2) is detected.

No particular limitation is imposed on the method for detecting the sandwich-like complex. For example, when the second polypeptide is labeled with a labeling substance, the complex can be detected by detecting the labeling substance.

Labeling substances may be detected by an appropriate method selected from among known methods established in accordance with the type of labeling substances. For example, when one component (e.g., biotin) of a certain specific binding pair is employed as a labeling substance, an enzyme (such as peroxidase) to which another component (e.g., streptavidin) capable of specifically binding to the first component is added, to thereby cause formation of a specific binding pair. Subsequently, a substrate (for example, hydrogen peroxide (in the case where the enzyme is peroxidase)) for the enzyme employed and a chromogenic substance (such as 3,3',5,5'-tetramethylbenzidine (TMB) or diaminobenzidine) is added, and color developed and assumed by the product of the enzymatic reaction is determined through absorptiometry, to thereby detect the labeled substance.

When a radioisotope, a fluorochrome, or a chemoluminescence substance serves as a labeling substance, radioactivity count, fluorescence intensity, fluorescence polarization, or luminescence intensity may be measured.

Through detection of such a labeling substance, the sandwich-like complex can be detected, attaining measurement of GAG of a single species (that is, a certain species of GAG) contained in the specimen. Because this method is a sandwich format, detection of a large amount of labeling substance indicates a commensurately large amount of a sandwich complex; in other words, presence of a large amount of GAG of a single species in the specimen.

When a qualitative assay of GAG (detection of the presence or absence of GAG) is desired, the results (positive or negative) regarding detection of the labeling substance is directly employed as the assay results for GAG.

When a quantitative assay of GAG (such as measurement of the GAG concentration) is desired, the absorbance value, radioactivity count, fluorescent intensity, or luminescence intensity may be directly employed as an index for the GAG content. Moreover, by use of standard GAGs of known concentrations, there may be prepared in advance calibration curves or correlation equations regarding the relation between GAG concentration and results of detection (e.g., absorbance) on standard substances, and the GAG concentration in the specimen may be determined therefrom. When a urine sample is employed as a specimen, the calculated GAG concentration may be corrected with reference to the concentrations of other substances (such as urine creatinine) contained in urine.

Another preferred method for the present invention is the inhibition method. That is, the method of the invention is preferably preformed through a method comprising the following steps (1) and (2):

(1) a step for forming first and second complexes by bringing "a third polypeptide capable of specifically binding to a GAG-containing molecule", "a specimen", and "a solid phase to which a GAG-containing molecule is immobilized" into contact with one another, the first complex being constituted by "GAG-containing molecule immobilized onto a solid phase—third polypeptide" and the second complex being constituted by "GAG-containing molecule in the specimen—third polypeptide"; and (2) a step for detecting at least one of the complexes formed in step (1), the first complex being "GAG-containing molecule immobilized onto a solid phase—third polypeptide" and the second complex being "GAG-containing molecule in the specimen—third polypeptide."

In step (1), the three substances; i.e., "a third polypeptide capable of specifically binding to a GAG-containing molecule", "a specimen", and "a solid phase to which a GAG-containing molecule is immobilized" may be brought into contact simultaneously. Alternatively, the former two substances may first be brought into contact with each other, followed by addition of the third substance for contact; or the latter two substances may first be brought into contact with each other, followed by addition of the first substance for contact. Preferably, according to the method of the present invention, the former two substances are first brought into contact with each other, followed by addition of the third substance for contact.

In step (2), of the first and second complexes, only the first complex (i.e., "GAG-containing molecule immobilized onto a solid phase—third polypeptide") or the second complex (i.e., "GAG-containing molecule in the specimen—third polypeptide"), or both, may be detected. According to the present method, detection of only the first complex is preferred.

That is, the method of the present invention preferably comprises the following steps (1) to (3):

(1) a step for forming a first complex by bringing "a third polypeptide capable of specifically binding to a GAG-containing molecule" and "a specimen" into contact, the first complex being constituted by "third polypeptide—GAG-containing molecule in the specimen";

(2) a step for forming a second complex by bringing "the solid phase to which a GAG-containing molecule is immobilized" into contact with a mixture resulting from step (1); i.e., a mixture containing "the first complex" and "a third polypeptide that has not participated in formation of the first complex", the second complex being constituted by "GAG-containing molecule immobilized onto the solid phase—third polypeptide"; and (3) a step for detecting the second complex formed in step (2).

Detection of the second complex is preferably carried out by use of a fourth polypeptide capable of specifically binding to the third polypeptide and having been labeled with, or being capable of being labeled with, a labeling substance.

Respective steps of the assay will next be described.

Step (1):

In step (1), a first complex is formed by bringing "a third polypeptide capable of specifically binding to a GAG-containing molecule" and "a specimen" into contact, the first complex being constituted by "third polypeptide—GAG-containing molecule in the specimen."

The description provided for the "third polypeptide capable of specifically binding to a GAG-containing molecule" also applies to the aforementioned "polypeptide capable of specifically binding to GAG (i.e., a GAG molecule itself)." Also, the specimen employed in this step is the same as that described above. No particular limitation is imposed on the manner of contact between the third polypeptide and the specimen, so long as the third polypeptide molecule can be brought into contact with a GAG-containing molecule contained in the specimen.

When the third polypeptide is brought into contact with the specimen, a first complex; i.e., a "third polypeptide—GAG-containing molecule in the specimen" is formed. As a result, step (1) can yield a mixture containing "the first complex" and "a third polypeptide that has not participated in formation of the first complex."

Step (2):

In step (2), the solid phase to which the GAG-containing molecule is immobilized is brought into contact with the mixture obtained from step (1); i.e., a mixture containing "the first complex" and "the third polypeptide that has not participated in formation of the first complex", to thereby form a complex of "GAG-containing molecule immobilized onto a solid phase—third polypeptide."

No particular limitation is imposed on the solid phase to which GAG-containing molecules are to be immobilized, so long as the solid phase is capable of immobilizing GAG-containing molecules and is insoluble in water, specimen, or reaction mixture of the assay. For other materials, see the descriptions provided hereinabove.

Also, the GAG-containing molecules capable of being immobilized onto the solid phase are the same as those described hereinabove. No particular limitation is imposed on the GAG-containing molecules capable of being immobilized onto the solid phase, so long as they have a site (or a portion) to which the third polypeptide can be specifically bound. That is, the GAG-containing molecule encompasses not only the GAG-containing molecule itself but also a fragment obtained through treatment of the GAG-containing molecule with a GAG-specific degradation enzyme.

GAG-containing molecules may be immobilized onto a solid phase through any conventional method, such as physical adsorption or covalent bonding. In particular, physical adsorption is preferred, from the viewpoints of convenience in procedure and prevalence in use.

The solid phase to which the GAG-containing molecules is immobilized is brought into contact with the mixture obtained in step (1) in a manner similar to that described above. Similar to the aforementioned case, preferably, the solid phase and liquid phase are separated from each other after completion of reaction, and in addition, in accordance with needs, non-specific adsorbents and the unreacted components remaining in the specimen are removed through washing of the surface of the solid phase with a washing solution. The washing solution which may be employed is as described in the foregoing.

By bringing the solid phase to which GAG-containing molecules is immobilized into contact with the mixture obtained from step (1), the "third polypeptides that have not participated in formation of the first complexes" are specifically bound to the GAG-containing molecules, to thereby form the complexes of the "GAG-containing molecules immobilized onto the solid phase—third polypeptides."

Step (3);

In step (3), the complexes formed in step (2) are detected.

No particular limitation is imposed on the method for detecting the complexes. However, detection is preferably performed by use of "fourth polypeptides capable of specifically binding to third polypeptides and having been labeled with, or being capable of being labeled with, a labeling substance."

No particular limitation is imposed on the "fourth polypeptides capable of specifically binding to third polypeptides" so long as the fourth polypeptides can specifically bind to the third polypeptides. When the third polypeptides are antibodies (immunoglobulins), the fourth polypeptides may be antibodies which can specifically bind to such immunoglobulins in accordance with the animals from which the immunoglobulins are derived or the class of the immunoglobulins. For example, when the third polypeptide is an immunoglobulin derived from mouse (mouse IgG1), en anti-mouse IgG1 antibody may nerve as the fourth polypeptide.

The descriptions provided for the previously mentioned labeling substance are also applicable to the labeling substance employable for labeling the fourth polypeptides. Preferably, the labeling substance is an enzyme (peroxidase, alkaline phosphatase, β-galactosidase, luciferase, acetylcholinesterase, glucose oxides, etc.), with peroxidase being more preferred.

Since the method for labeling the fourth polypeptides with a labeling substance and the method for detecting the labeling substance are performed in manners similar to those described hereinabove, descriptions therefor are omitted for the sake of simplicity. However, since the employed method is the inhibition method, detection of a large amount of the labeling substance should be interpreted such that the amount of the "third polypeptides that have not participated in formation of 'third polypeptide—GAG-containing molecule in the specimen' complexes" is commensurably large (that is, the amount of the complexes being commensurably small); in other words, the amount of the GAG of a single species contained in the specimen is small.

In the present invention, no particular limitation is imposed on the "lysosomal storage diseases" which are to be detected by the present method and are correlated with assay results of GAGs, so long as the "lysosomal storage diseases" are diseases recognized as such in the art. Preferably, the "lysosomal storage diseases" are at least one disease selected from mucopolysaccharidoses, mucolipidoses, GM1 gangliosidoses, fucosidoses, galactosialidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses.

In the present invention, no particular limitation is imposed on the "mucopolysaccharidoses" which are to be detected by the present method and are correlated with assay results of GAGs, so long as the "mucopolysaccharidoses" are diseases recognized as such in the art. Preferably, the "mucopolysaccharidoses" are a class of mucopolysaccharidosis types I, II, III, IV, VI, and VII.

In the present invention, no particular limitation is imposed on the "mucolipidoses", "GM1 gangliosidoses", "fucosidoses", "galactosialidoses", "metachromatic leukodystropy", "Niemann-Pick diseases", "Tay-Sachs disease", "Sandhoff disease", "GM2 gangliosidoses", "Krabbe disease", "Fabry disease", "Gaucher diseases", "glycogen storage diseases" and "lipofuscinoses" so long as they are diseases recognized as such in the art. Preferably, the "mucolipidoses" are mucolipidosis types II or III. Preferably, the "Niemann-Pick diseases" are Niemann-Pick disease types B or C. Preferably, the "Gaucher diseases" are Gaucher disease types I or III. Preferably, the "glycogen storage diseases" are glycogen storage disease types 1 or 2.

The step in which lysosomal storage diseases are correlated with assay results of GAGs may be performed as follows.

As described above, a specimen from an animal of lysosomal storage diseases shows a significantly high GAG level. Accordingly, when the measurement of GAG of a single species (GAG level) is higher than that (GAG level) of healthy animals (animals of non-lysosomal storage diseases), the measurement can be correlated to "affirmation of lysosomal storage diseases" or "high risk of lysosomal storage diseases"

When the measurement of GAG of a single species (GAG level) is lower than that (GAG level) of healthy an the measurement can be correlated to "free of lysosomal storage diseases" or "low risk of lysosomal storage diseases"

The correlation between the identified GAG level and lysosomal storage diseases encompasses not only that for predicting the "presence or absence of the risk of lysosomal storage diseases" but also that for predicting the severity or progress of lysosomal storage diseases. For example, if the GAG level of a specimen obtained from a certain individual is periodically measured and shows a tendency of increase in the GAG level, such a tendency may be correlated to "progressive lysosomal storage diseases" or "high risk of lysosomal storage diseases progressing." On the other hand, when the results show a tendency of decrease in the GAG level, such a tendency may be correlated to "lysosomal storage diseases ameliorating" or "high possibility of lysosomal storage diseases ameliorating." Also, when no changes in the GAG level are observed, this can be correlated to "no changes in the state of lysosomal storage diseases" or "high possibility of lysosomal storage diseases neither progressing nor mitigating."

The measurement (GAG level) which forms the basis for the correlation with lysosomal storage diseases may be the GAG concentration obtained by use of the aforementioned calibration curve or the correlation equations, or the GAG ratio with respect to the GAG level as determined in a specimen from healthy animals.

According to the method of the present invention, the "GAG of a single species" is preferably a GAG having a sulfate group. More preferably, the GAG having a sulfate group is KS, and simultaneously, the "mucopolysaccharidoses" to be detected are one or more mucopolysaccharidoses selected from mucopolysaccharidosis types I, II, III, VI, and VII. This is a particularly important feature of the present invention, since the finding that KS is secreted into body fluids of a subject suffering mucopolysaccharidosis type I, II, III, VI or VII has remained completely unknown until conception of the present invention. Among the above types, the "mucopolysaccharidoses" to be detected are preferably one or more mucopolysaccharidoses selected from types I, II, III and VI. The "GAG having a sulfate group" is preferably KS, and simultaneously, the "mucolipidoses" to be detected are one or more mucolipidoses selected from mucolipidoses types II and III.

In the present invention, the following case is also preferred: The GAG having a sulfate group is HS, and simultaneously, the "mucopolysaccharidoses" to be detected are one or more mucopolysaccharidoses selected from mucopolysaccharidosis types IV and VI. This is also a particularly important feature of the present invention, since the finding that HS is secreted into body fluids of subjects suffering mucopolysaccharidosis type IV or VI has remained completely unknown until conception of the present invention.

In the present invention, the following case is also preferred: the GAG having a sulfate group is HS, and the lysosomal storage diseases are of one or more diseases selected from among mucolipidoses, metachromatic leukodystropy, Niemann-Pick diseases, Tay-Sachs disease, Sandhoff disease, GM2 gangliosidoses, Krabbe disease, Fabry disease, Gaucher diseases, glycogen storage diseases and lipofuscinoses.

In the present invention, the following case is also Preferred: The GAG having a sulfate group is CS, and simultaneously, the "mucopolysaccharidoses" to be detected are one or more mucopolysaccharidoses selected from mucopolysaccharidosis types I, II, III, IV, and VI. This is also a particularly important feature of the present invention, since the finding that CS is secreted into body fluids of subjects suffering mucopolysaccharidosis of the above types has remained completely unknown until conception of the present invention.

In the present invention, the following case is also preferred: The GAG having a sulfate group is DS, and simultaneously, the "mucopolysaccharidosis" to be detected are one or more mucopolysaccharidoses selected from mucopolysaccharidosis types III and IV. This is also a particularly important feature of the present invention, since the finding that DS is secreted into body fluids of subjects suffering mucopolysaccharidosis of the above types has remained completely unknown until conception of the present invention.

Although the descriptions hereinabove have focused on the "detection method" for lysosomal storage diseases, the method of the present invention is not necessarily limited only to such a method, and a "screening method" and a "diagnosis method" are also envisaged by the present invention.

<2> Kit of the Present Invention

The kit of the present invention includes the following components, and is intended to be used to detect at least one disease selected from mucopolysaccharidoses, mucolipidoses, GM1 gangliosidoses, fucosidoses, galactosialidoses, metachromatic leukodystropy, Niemann-Pick disease, Tay-Sachs disease, Sandhoff disease, GM2 gangliosidoses, Krabbe disease, Fabry disease, Gaucher disease, glycogen storage disease and lipofuscinoses on the basis of the measurement of GAG of a single species in a specimen:

(A) a solid phase to which a first polypeptide capable of specifically binding to a GAG-containing molecule is immobilized; and (B) a second polypeptide capable of specifically binding to a GAG-containing molecule and having been labeled with, or being capable of being labeled with, a labeling substance.

In the following descriptions of the kit of the present invention, the terms "GAG of a single species", "first polypeptide capable of specifically binding to a GAG-containing molecule", "solid phase to which a first polypeptide is immobilized", "second polypeptide capable of specifically binding to a GAG-containing molecule", "labeling substance", method for labeling a polypeptide with a labeling substance, and target "mucopolysaccharidoses, etc." to be detected all have the same meanings as previously provided in section <1> Method of the Present Invention. The present kit can be used to detect lysosomal storage diseases through sandwich assay of GAGs.

Instead of the above components (A) and (B), the kit of the present invention may include the following components (A), (B), and (C):

(A) a solid phase to which a GAG-containing molecule is immobilized, (B) a third polypeptide capable of specifically binding to a GAG-containing molecule, and (C) a fourth polypeptide capable, of specifically binding to the third polypeptide and having been labeled with, or being capable of being labeled with, a labeling substance.

In the following descriptions of the kit of the present invention, the terms "solid phase to which a GAG-containing molecule is immobilized", "third polypeptide capable of specifically binding to a GAG-containing molecule", "fourth polypeptide capable of specifically binding to a third polypeptide", "labeling substance", "method for labeling a polypeptide with a labeling substance, and target "mucopolysaccharidoses, etc." to be detected all have the same meanings as previously provided in section <1> Method of the Present Invention. The present kit can be used to detect mucopolysaccharidoses, etc. through the inhibition assay of GAGs.

Detection of mucopolysaccharidoses, etc. by use of any mode of the kit of the present invention can be achieved in accordance with the descriptions provided in section <1> Method of the Present Invention."

In the kit of the present invention, the "polypeptide" is preferably an antibody or a polypeptide having an antigen binding site of an antibody.

No particular limitation is imposed on the "mucopolysaccharidoses" which are to be detected by the present kit, so long as the "mucopolysaccharidoses" are diseases recognized as such in the art. Preferably, the "mucopolysaccharidoses" axe a class of mucopolysaccharidosis types I, II, III, IV, VI, and VII. In the same manner, in the kit of the present invention, no particular limitation is imposed on the "mucolipidoses", "GM1 gangliosidoses", "fucosidoses", "galactosialidoses", "metachromatic leukodystropy", "Niemann-Pick diseases", "Tay-Sachs disease", "Sandhoff disease", "GM2 gangliosidoses", "Krabbe disease", "Fabry disease", "Gaucher diseases", "glycogen storage diseases" and "lipofuscinoses", so long as they are diseases recognized as such in the art. Preferably, the "mucolipidoses" are mucolipidosis type II or III. Preferably, the "Niemann-Pick diseases" are Niemann-Pick disease types B or C. Preferably, the "Gaucher diseases" are Gaucher disease types I or III. Preferably, the "glycogen storage diseases" are glycogen storage disease types 1 or 2.

Moreover, "GAG of a single species" in the kit of the present invention is preferably a GAG having a sulfate group, and the GAG having a sulfate group is preferably KS, HS, CS, or DS.

In the kit of the present invention, the "GAG having a sulfate group" is preferably KS, and simultaneously, the "mucopolysaccharidoses" are one or more mucopolysaccharidoses selected from mucopolysaccharidosis types I, II, III, VI, and More preferably, the "mucopolysaccharidoses" to be detected are one or more mucopolysaccharidoses selected from mucopolysaccharidosis types I, II, III, and VI. Also, the "GAG having a sulfate group" is preferably KS, and simultaneously, the "mucolipidoses" are one or more mucolipidoses selected from mucolipidosis types II and III.

Moreover, the following cases are also preferred: The "GAG having a sulfate group" is HS, and simultaneously, the "mucopolysaccharidoses" are one or more mucopolysaccharidoses selected from mucopolysaccharidosis types IV and VI; the "GAG having a sulfate group" is HS, and the lysosomal storage diseases are of one or more diseases selected from among mucolipidoses, metachromatic leukodystropy, Niemann-Pick diseases, Tay-Sachs disease, Sandhoff disease, gangliosidoses, Krabbe disease, Fabry disease, Gaucher diseases, glycogen storage diseases and lipofuscinoses; the "GAG having a sulfate group" is CS, and simultaneously, the "mucopolysaccharidoses" are one or more mucopolysaccharidoses selected from mucopolysaccharidosis types I, II, III, IV and VI; the "GAG having a sulfate group" is DS, and simultaneously, the "mucopolysaccharidoses" are one or more mucopolysaccharidoses selected from mucopolysaccharidosis types III and IV. Note that these features also apply to the method of the present invention.

No particular limitation is imposed on the kit of the present invention, so long as the kit includes the above-described components. The kit may further include standard GAG products of known concentration serving as standard samples useful for drawing calibration curves or establishing correlation equations, detection reagents for labeling substances, and so on. In addition to these components, the kit may also include the aforementioned blocking substance, the aforementioned washing solution, a solution for diluting specimens, and a solution for stopping enzymatic reactions. Moreover, the kit may include a substance serving as a positive control (QC-control), which is used to maintain a certain assay level throughout the assay batches.

These components may be individually stored in separate containers forming a kit, which is subsequently used according to the method of the present invention.

Although the above description has focused on a "detection kit" for mucopolysaccharidoses, needless to say, a "screening kit" and a "diagnosis kit" are also envisaged by the present invention.

BEST MODE FOR CARRYING OUT THE INVENTION

Figure 1:
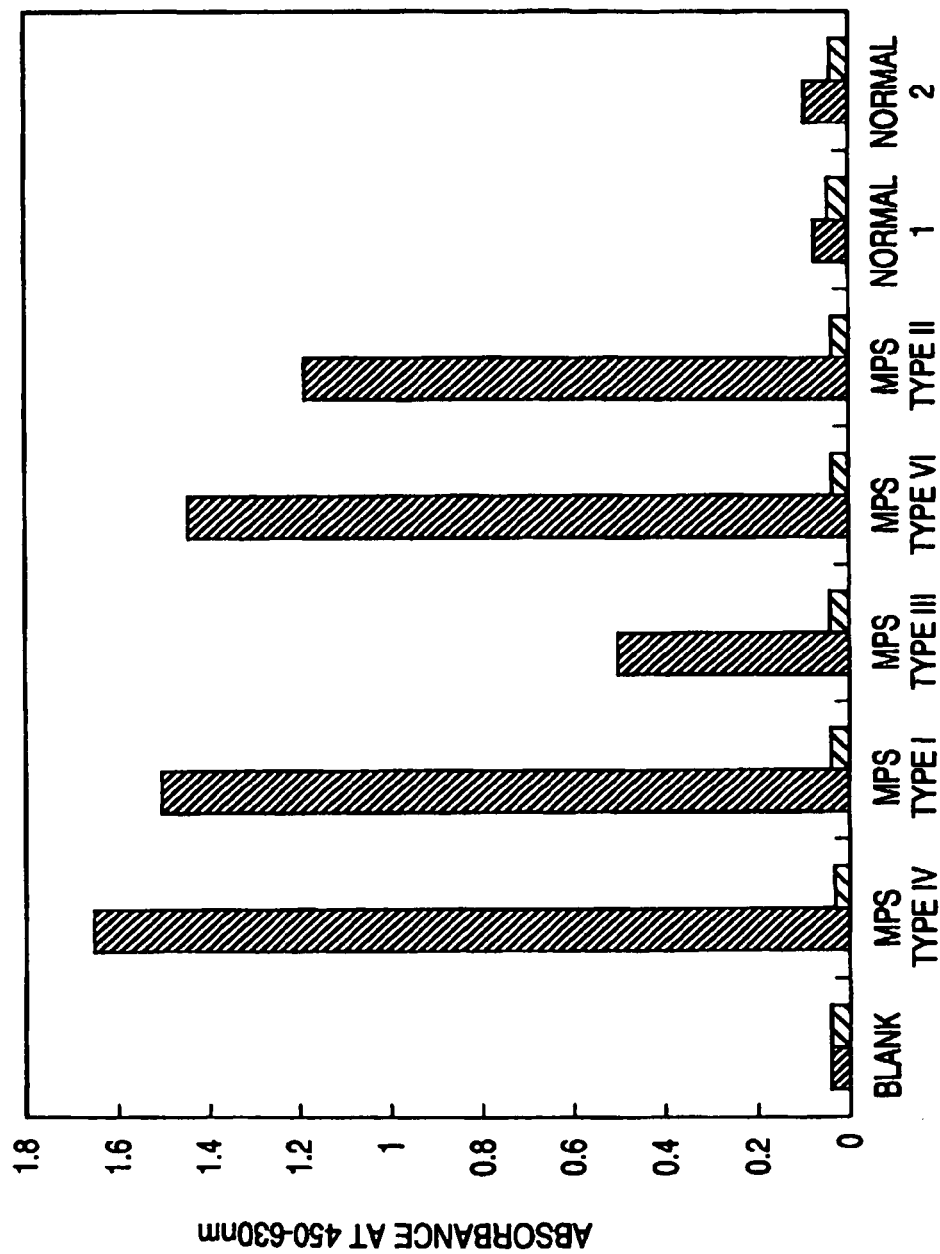
FIG. 1 is a graph showing the KS levels determined in human urine specimens.

The present invention will next be described in more detail by way of examples, which should not be construed as limiting the invention thereto.

EXAMPLE 1

A sandwich assay was performed to detect mucopolysaccharidoses in human urine samples.
(1) The Specimens, Reagents, Etc. Employed in Example 1 were as Follows.
Specimens and Standard Samples:
  The specimens were human urine samples collected from patients suffering human mucopolysaccharidosis types I, II, III, IV, or VI (1 subject each) and healthy humans (humans not suffering mucopolysaccharidosis; 2 subjects).
The Standard GAGs Employed were as Follows:
* HS (derived from bovine kidney, produced by Seikagaku Corporation):
  This KS is available from Seikagaku Corporation as reagent catalogue code No. 400700, and has the following properties.
Nitrogen Content:
  2.6 to 3.2% (measured by the method described in Z. Anal. Chem., 22, 366 (1883))
Sulfur Content:
  5.0 to 6.0% (measured by the method described in Mikrochim. Acta., 123 (1955))
Uronic Acid Content:
  28.0 to 30.0% (oxynol reaction)
  36.0 to 40.0% (carbazole reaction)
Glucosamine Content:
  30.0 to 35.0% (amino acid automatic analyzer)
Galactosamine Content:
  <0.01%
* KS (keratan polysulfate; derived from shark cartilage; produced by Seikagaku Corporation):
  This KS is contained in a kit available from Seikagaku Corporation as reagent catalogue code No. 400610, and has the following properties.
Nitrogen Content:
  2.58% (measured by the method described in Z. Anal. Chem., 22, 366 (1883))
Sulfur Content:
  9.70% (measured by the method described in Mikrochim. Acta., 123 (1955))
Glucosamine Content:
  23.51% (amino acid automatic analyzer)
Galactosamine Content:
  0.11% (amino acid automatic analyzer)
Galactose Content:
  26.26% (Biochem. J., 50, 298 (1952))
* CS (chondroitin sulfate D; derived from shark cartilage; produced by Seikagaku Corporation):
  This CS is available from Seikagaku Corporation as reagent catalogue code No. 400676, and has the following properties.
Nitrogen Content:
  2.2 to 2.6% (measured by the method described in Z. Anal. Chem., 22, 366 (1883))
Sulfur Content:
  7.1 to 7.7% (measured by the method described in Mikrochim. Acta., 123 (1955))
Galactosamine Content:
  30 to 35% (amino acid automatic analyzer)
Glucuronic Acid Content:
  32 to 35% (carbazole reaction)
  Chondroitin sulfate D is a molecule in which "disaccharide units in which a glucuronic acid residue and an N-acetylgalactosamine residue are bound via $\beta$1,3-glycoside linkage" are continuously bound, and CS containing, as a main constitution component, a disaccharide unit consisting of "a glucuronic acid residue sulfated at the 2-position and an N-acetylgalactosamine residue sulfated at the 6-position."
* Decorin (derived from bovine articular cartilage; produced by Sigma)
Antibodies:
  "5D4" (produced by Seikagaku Corporation) was employed to serve as an anti-KS antibody to be immobilized onto a solid phase. "Biotinylated 5D4" (produced by Seikagaku Corporation) was employed to serve as a biotinylated anti-KS antibody.
  "F58-10E4" (produced by Seikagaku Corporation) was employed to serve as an anti-HS antibody to be immobilized onto a solid phase. "Biotinylated F58-10E4" (produced by Seikagaku Corporation) was employed to serve as a biotinylated anti-HS antibody.
  "LY111" (produced by Seikagaku Corporation) was employed to serve as an anti-CS antibody to be immobilised onto a solid phase. "Biotinylated LY111" (produced by Seikagaku Corporation) was employed to serve as a biotinylated anti-CS antibody.
  "6-B-6" (produced by Seikagaku Corporation) was employed to serve as an antibody for the core protein of proteoglycan (decorin).
Antibody-Immobilized Plates:
  The antibody-immobilized plates (i.e., plates to which "5D4", "F58-10E4", "LY111", or "6-B-6" antibodies were immobilized) were prepared as described below.
  Antibodies of each of the above species were dissolved in phosphate buffered saline (PBS), to thereby adjust protein concentration to 20 µg/ml. The solution was added to an immunoplate (MAXISORP; produced by Nunc) in an amount of 50 µl/well, followed by incubation at 37° C. for 1.5 hours.
  After completion of incubation, the wells were washed twice with PBS, and the blocking substance (Immunoassay Stabilizer; produced by Applied Biosystems) was added to each well in an amount of 200 µl/well. Subsequently, the wells were incubated at 37° C. for 1 hour.
  The thus-prepared antibody-immobilized plates, when washed with a washing solution 3 times, are ready to use, and can also be used even after storage for several months following drying.
Reagents, etc.:
  Washing solution: PBS containing 0.05% Tween 20
  Specimen diluting solution: PBS(−) containing 1% bovine serum albumin (BSA)
(2) Detection of Mucopolysaccharidoses Through Measurement of KS
  Each specimen was diluted with specimen diluting solution, to thereby prepare two sets of diluted specimens (0.5 ml each). To each specimens of a first set, keratanase II (2.5 mU, produced by Seikagaku Corporation) was added, whereas this enzyme was not added to the specimens of the other set. Subsequently, all the specimens were incubated at room temperature for 3 hours.

The incubated specimens (which may be called "assay specimens") were subjected to a GAG assay as described below, by use of the 5D4-immobilized plate and biotinylated 5D4.

Each of the assay specimens was added to the wells of the respective antibody-immobilized plates described above in an amount of 50 μl/well, followed by incubation at 37° C. for 1 hour. Subsequently, washing solution was added to the wells in an amount of 200 μl/well, and the plates were washed 4 times.

Biotinylated 5D4 was diluted with specimen diluting solution so as to attain a concentration of 0.5 μg/ml, and then was added to the wells of each antibody-immobilized plate in an amount of 50 μl/well, followed by incubation at 37° C. for 1 hour. Subsequently, washing solution was added to the wells in an amount of 200 μl/well, and the plates were washed 4 times.

Avidin-peroxidase (produced by Vector) was subjected to 1,000-fold dilution by use of specimen diluting solution, and then added to the wells of each antibody-immobilized plate in an amount of 50 μl/well, followed by incubation at 37° C. for 30 minutes. Subsequently, washing solution was added to the wells in an amount of 200 μl/well, and the plates were washed 4 times.

A TMB solution (substrate, produced by Moss Inc.) was added to the wells of each plate in an amount of 50 μl/well, then subjected to incubation at room temperature for 5 minutes. Next, 1 M HCl was added thereto in an amount of 50 μl/well, to thereby stop enzymatic reaction. The absorbance at 450-630 nm was measured by use of an absorptiometer.

The measurement results of absorbance are shown in FIG. 1. The left bars of each bar set show the results obtained from the solutions that had not undergone any treatment with keratanase II, whereas the right bars show the results obtained from the solutions that had undergone treatment with keratanase II. In FIGS. 1 to 4, "Blank", "MPS", and "Normal" indicate the results corresponding to no specimen being added, mucopolysaccharidosis, and healthy subjects, respectively.

As shown in FIG. 1, urine samples collected from subjects suffering any of mucopolysaccharidosis types I to VI were found to exhibit significantly high absorbance values as compared with the urine samples collected from healthy subjects. Specimens treated with keratanase II (which specifically degrades KS) exhibited low absorbance values, which are on similar levels. These results indicate that high absorbance values exhibited in urine samples from subjects suffering any of mucopolysaccharidosis types I to VI are attributed to KS; in fact, in all the urine samples from the subjects suffering mucopolysaccharidosis of any type, the amount of KS was found to be significantly high. Particularly, high KS levels in urine samples of mucopolysaccharidosesis types I, II, III, and VI are surprising, because such high data have never been expected.

Thus, it has now been shown that mucopolysaccharidoses can be detected by correlating the assay results of GAG of a single species (in this case, KS) contained in body fluid (urine) with mucopolysaccharidoses.

(3) Detection of Mucopolysaccharidoses Through Measurement of HS

Each specimen was diluted with specimen diluting solution, to thereby prepare two sets of diluted specimens (0.5 ml each). To each specimen of a first set, heparitinase I (10 mU, produced by Seikagaku Corporation) was added, whereas this enzyme was not added to the specimens of the other set. Subsequently, all the specimens were incubated at room temperature for one hour. The standard samples (HS) also underwent similar treatment.

The incubated specimens (which may be called "assay specimens") were subjected to a GAG assay as described below, by use of an F58-10E4-immobilized plate and biotinylated F58-10E4.

Each of the assay specimens was added to the wells of the respective antibody-immobilized plates described above in an amount of 50 μl/well, followed by incubation at 37° C. for 1 hour. Subsequently, washing solution was added to the wells in an amount of 200 μl/well, and the plates were washed 4 times.

Avidin-peroxidase (produced by Vector) diluted 1,000-fold with specimen diluting solution (4° C.) and biotinylated F58-10E4 diluted with a specimen diluting solution (4° C.) to attain a concentration of 1.0 μg/ml were added to the wells of each antibody-immobilized plate in an amount of 25 μl/well each, followed by incubation at 4° C. for 1 hour. Subsequently, washing solution was added to the wells in an amount of 200 μl/well, and the plates were washed 4 times.

The steps from addition of TMB solution (substrate) up to measurement of absorbance were the same as those described in (2) above.

Figure 2:
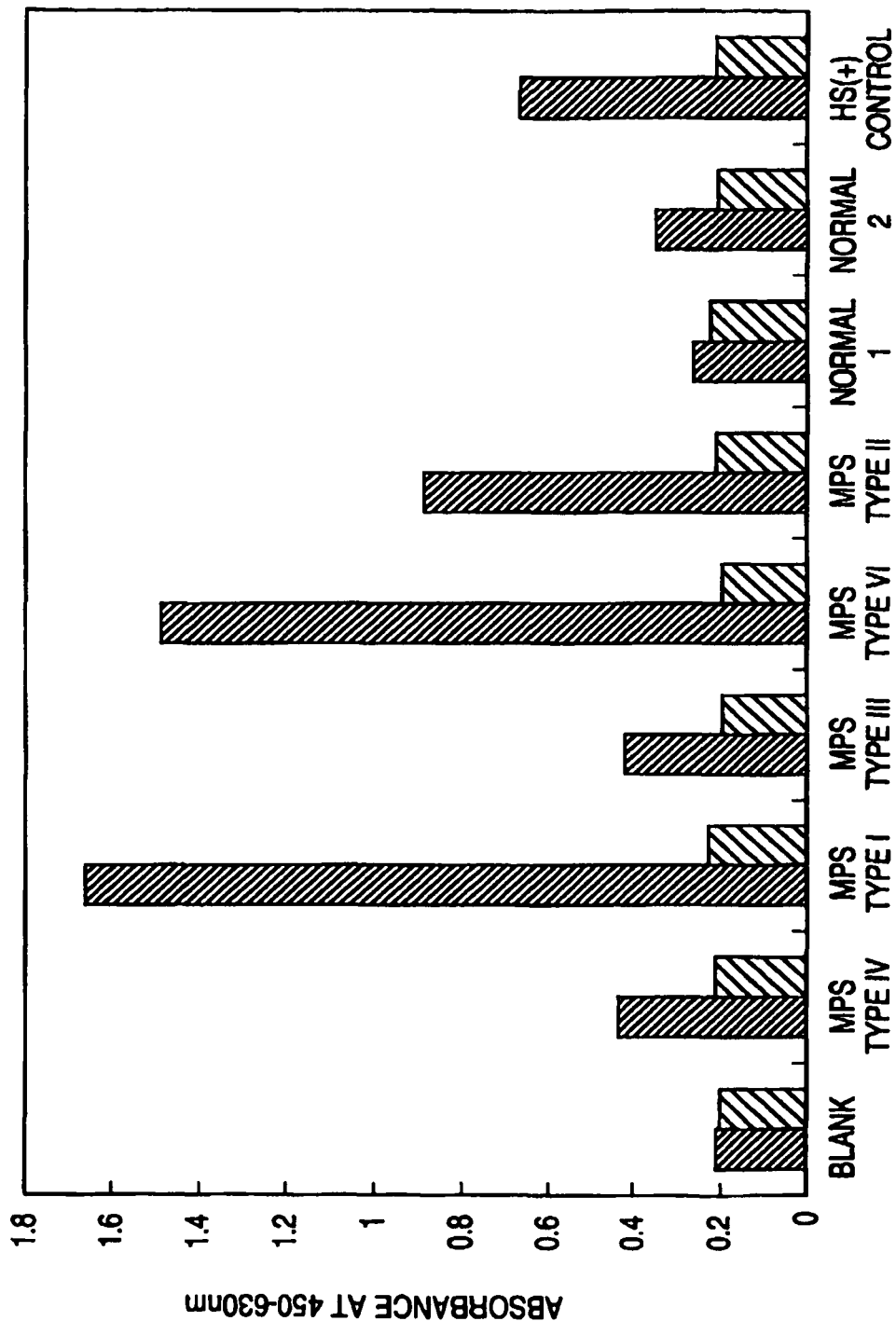
FIG. 2 is a graph showing the HS levels determined in human urine specimens.

The measurement results of absorbance are shown in FIG. 2. The left bars of each bar set show the results obtained from the solutions that had not undergone any treatment with heparitinase I, whereas the right bars show the results obtained from the solutions that had undergone treatment with heparitinase I, "HS(+) control" indicates the results obtained from the cases where standard samples (HS) were employed.

As shown in FIG. 2, urine samples collected from subjects suffering any of mucopolysaccharidosis types I to VI were found to exhibit significantly high absorbance values as compared with the urine samples collected from healthy subjects. Specimens treated with heparitinase I (which specifically degrades HS) exhibit low absorbance values, which are on similar levels. These results indicate that high absorbance values exhibited in urine samples from subjects suffering any of mucopolysaccharidosis types I to VI are attributed to HS; in fact, in all the urine samples from the subjects suffering any of mucopolysaccharidosis of any type, the amount of HS was found to be significantly high. Particularly, high HS values in urine samples of mucopolysaccharidosis types IV and VI are surprising, because such high data have never been expected.

Thus, it has now been shown that mucopolysaccharidoses can be detected by correlating the assay results of GAG of a single species (in this case, HS) contained in body fluid (urine) with mucopolysaccharidoses.

(4) Detection of Mucopolysaccharidoses Through Measurement of CS

Each specimen was diluted with specimen diluting solution, to thereby prepare diluted specimens (0.5 ml each).

The diluted specimens (which may be called "assay specimens") were subjected to a GAG assay as described below, by use of an LY111-immobilized plate and biotinylated LY111.

Each of the assay specimens was added to the wells of the respective antibody-immobilized plates described above in an amount of 50 μl/well, followed by incubation at 37° C. for 1 hour. Subsequently, washing solution was added to the wells in an amount of 200 μl/well, and the plates were washed 4 times.

Avidin-peroxidase (produced by Vector) diluted 1,000-fold with specimen diluting solution (4° C.) and biotinylated LY111 diluted with a specimen diluting solution (4° C.) to attain a concentration of 1.0 μg/ml were added to the wells of each antibody-immobilized plate in an amount of 25 µl/well each, followed by incubation at 37° C. for 1 hour. Subsequently, washing solution was added to the wells in an amount of 200 µl/well, and the plates were washed 4 times.

The steps from addition of TMB solution (substrate) up to measurement of absorbance were the same as those described in (2) above. The results of absorptiometry are shown in FIG. 3.

Figure 3:
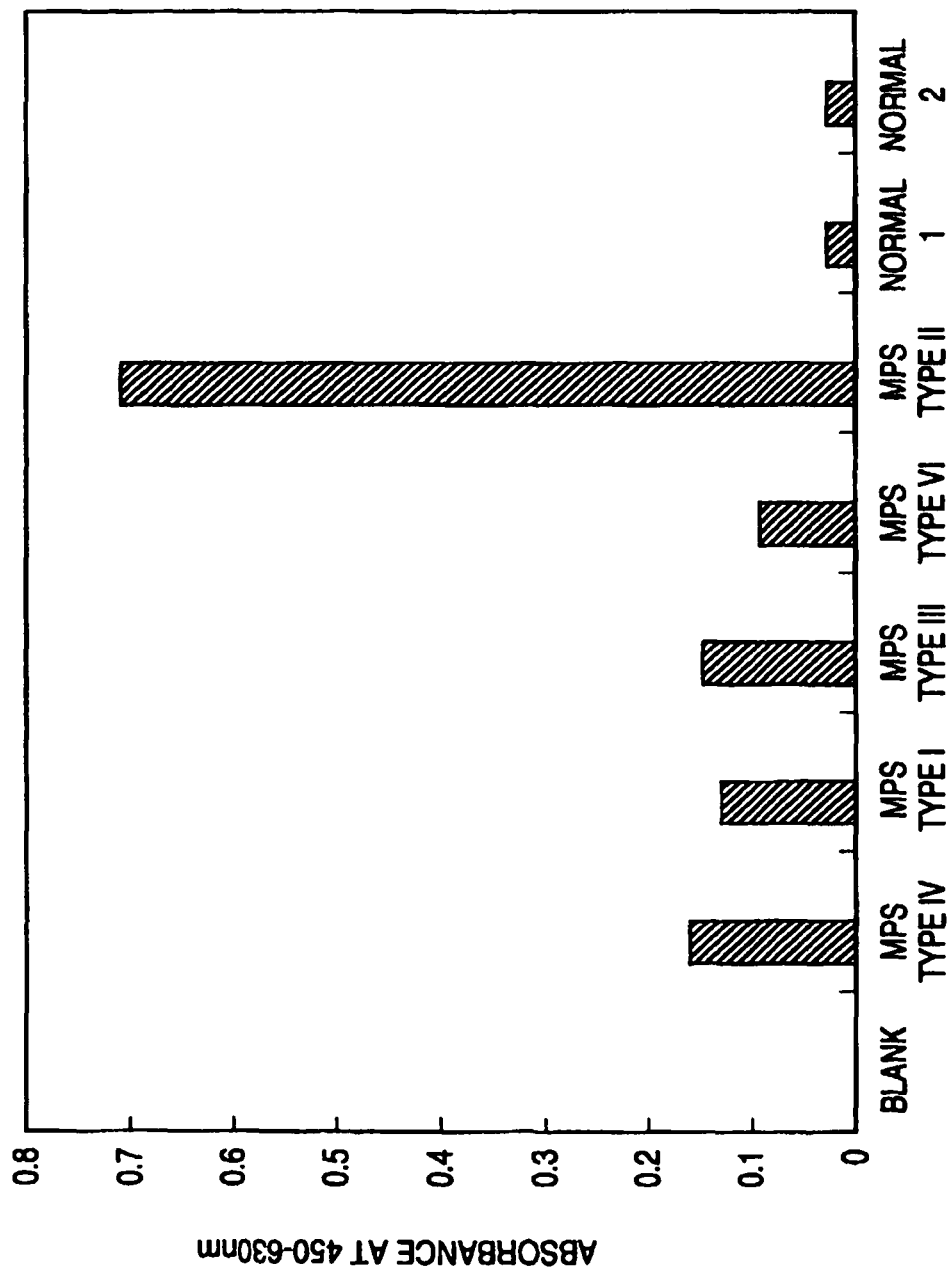
FIG. 3 is a graph showing the CS levels determined in human urine specimens.

As shown in FIG. 3, urine samples collected from subjects suffering any of mucopolysaccharidosis types I to VI were found to exhibit high absorbance values as compared with urine samples collected from healthy subjects. These results indicate that high CS values exhibited in urine samples from subjects suffering any of mucopolysaccharidosis types I to VI are attributed to CS. Particularly, high CS values in urine samples of mucopolysaccharidosis types I, II, III, IV, and VI are surprising, because such high data have never been expected.

Thus, it has now been shown that mucopolysaccharidoses can be detected by correlating assay results of GAG of a single species (in this case, CS) contained in body fluid (urine) with monopolysaccharidoses.

(5) Detection of Mucopolysaccharidoses Through Measurement of DS

Each specimen was diluted with specimen diluting solution, to thereby prepare diluted specimens (0.5 ml each).

The diluted specimens (which may be called "assay specimens") were subjected to a GAG assay as described below, by use of the 6-B-6-immobilized plate and biotinylated LY111. "6-B-6" is an antibody capable of specifically binding to the core protein of proteoglycan (decorin). Accordingly, the target GAG to be measured is DS present in the proteoglycan (decorin) molecule.

Each of the assay specimens was added to the wells of the respective antibody-immobilized plates described above in an amount of 50 µl/well, followed by incubation at 37° C. for 1 hour. Subsequently, washing solution was added to the wells in an amount of 200 µl/well, and the plates were washed 4 times.

Avidin-peroxidase (produced by Vector) diluted 1,000-fold with specimen diluting solution (4° C.) and biotinylated LY111 diluted with a specimen diluting solution (4° C.) to attain a concentration of 1.0 µg/ml were added to the wells of each antibody-immobilized plate in an amount of 25 µl/well each, followed by incubation at 37° C. for 1 hour. Subsequently, washing solution was added to the wells in an amount of 200 µl/well, and the plates were washed 4 times.

The steps from addition of TMB solution (substrate) up to measurement of absorbance were the same as those described in (2) above. The results of absorptiometry are shown in FIG. 3.

Figure 4:
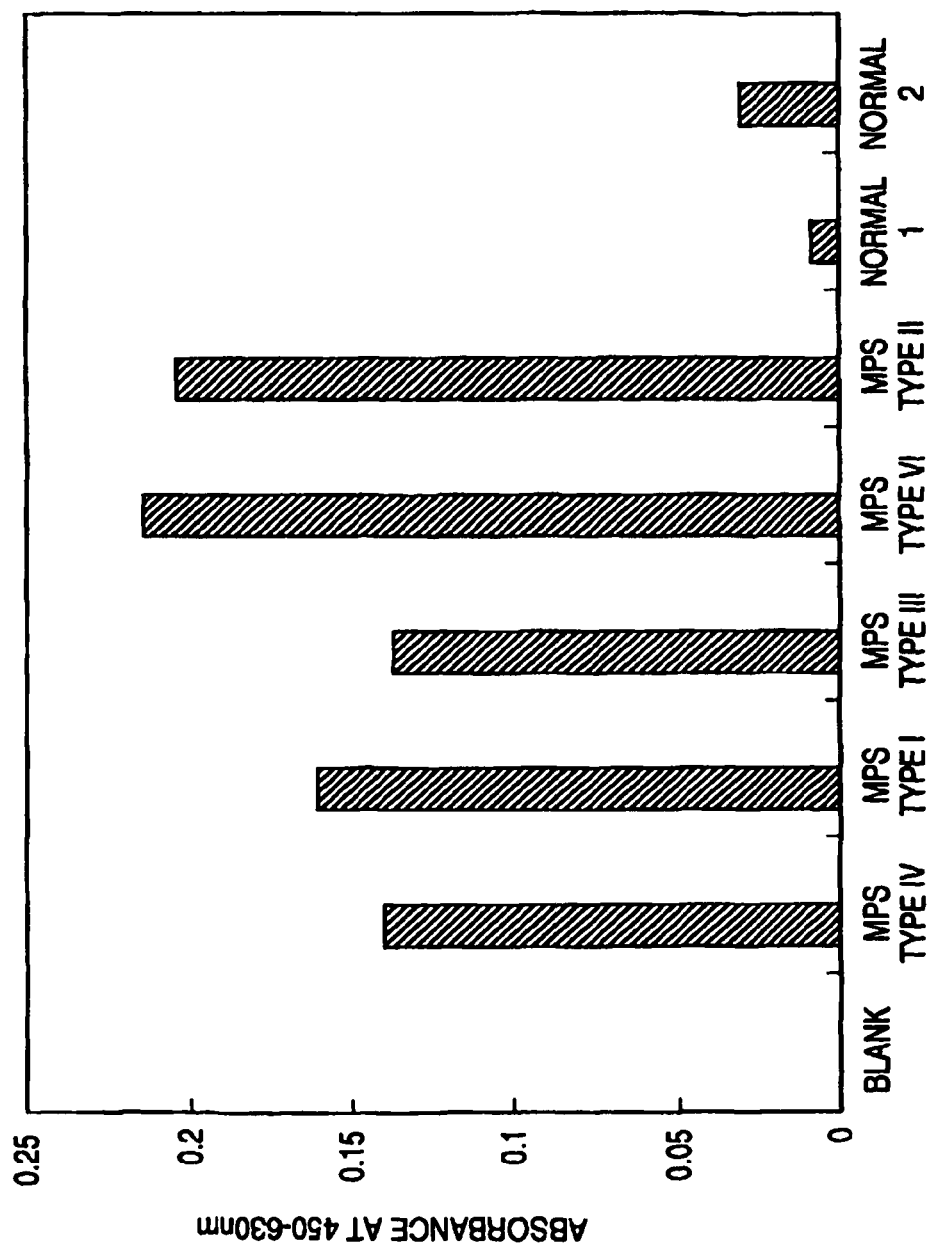
FIG. 4 is a graph showing the DS levels determined in human urine specimens.

As shown in FIG. 4, urine samples collected from subjects suffering any of mucopolysaccharidosis types I to VI were found to exhibit significantly high absorbance as compared with the urine samples collected from healthy subjects. These results indicate that high DS values exhibited in urine samples from subjects suffering mucopolysaccharidosis types I to VI are attributed to DS. Particularly, high DS values in urine samples of mucopolysaccharidosis types III and IV are surprising, because such high data have never been expected.

Thus, it has now been shown that mucopolysaccharidoses can be detected by correlating the assay results of GAG of a single species (in this case, DS) contained in body fluid (urine) with mucopolysaccharidoses.

EXAMPLE 2

An inhibition assay was performed to detect mucopolysaccharidoses in serum or urine samples from dogs or cats.

(1) Specimens, Reagents, Etc. Employed in Example 2 are as Follows.

Specimens:

The specimens employed are serum and urine samples collected from mucopolysaccharidosis type IIIB or VII model animals (dogs); mucopolysaccharidosis type I, VI, or VII model animals (cats); and healthy animals (dogs and cats not suffering mucopolysaccharidosis).

The standard GAG employed is KS derived from bovine cornea (Sigma Co.).

Antibodies:

The primary antibody employed is anti-KS antibody "5D4" (1/20/5D4; ICN Immunobiologicals). The secondary antibody employed is horseradish-peroxidase-bound anti-mouse IgG (H+L) (Pierce Co.).

Antigen-Immobilized Plate:

An antigen-immobilized plate (i.e., a plate to which KS is immobilized) was prepared as described below.

0.2 U Chondroitinase ABC (produced by Seikagaku Corporation) was added to 1 mg KS solution (bovine-cornea-derived KS; Sigma), and the resultant solution was incubated (2 hours, 37° C.) under shaking, to thereby degrade contaminants such as CS. After treatment with Chondroitinase ABC, the KS solution was diluted and added to the wells of an immunoplate (produced by Nunc) in an amount of 200 µl/well, followed by incubation for 2 hours at roam temperature.

The thus-prepared antigen-immobilized plate can be used immediately after washing, and can also be used even after storage for one month or thereabouts at 4° C.

Reagents, Etc.:

Washing solution: PBS containing 0.05% Tween 20 (pH 5.3)

Specimen Diluting Solution:

PBS containing 1% BSA and 0.05% Tween 20 (pH 5.3)

(2) Detection of Mucopolysaccharidoses Through Measurement of KS

A specimen (serum or urine) was added to an immunoplate to which no antigens were immobilized, and the specimen was diluted to 140 µl/well with specimen diluting solution, followed by addition of a primary antibody solution (140 µl/well) diluted with specimen diluting solution so as to attain a concentration of 1/18,000 the original concentration. The thus-prepared plate was incubated overnight at 4° C.

The wells of the antigen-immobilized plate were washed three times with washing solution, and to the thus-washed wells was added the incubated specimen mixture (which had undergone reaction with primary antibodies) in an amount of 200 µl/well, followed by incubation at 4° C. for one hour. Subsequently, the wells were washed three times with washing solution.

The secondary antibody solution diluted 1,000-fold with specimen diluting solution was added to the specimen mixture in an amount of 200 µl/well. The specimen mixture was incubated at room temperature for one hour under shaking. Subsequently, the wells were washed three times with washing solution.

A TMB solution (substrate, Moss Inc.) was added to the walls of the plate in an amount of 200 µl/well, and under observation of developing color of the mixture, the plate was incubated at room temperature. Enzymatic reaction of the mixture was stopped by adding 2M HCl (50 µl/well), and the absorbance at 490 nm was measured by use of an absorptiometer. The concentration of KS was obtained through use of the absorbance data and the calibration curve which had been prepared in advance from the absorbance data of the standard sample. The results from the urine specimens are shown below. The values in parentheses are those corrected with respect to the concentration of creatinine (Cre).

Urine:

| Healthy dogs | 121.38 ng/ml | (132.49 ng/mg Cre) |
| MPS type IIIB dogs | 380.52 ng/ml | (345.85 ng/mg Cre) |
| MPS type VII dogs | 1988.28 ng/ml | (435.07 ng/mg Cre) |
| MPS type I cats | 3150.90 ng/ml | (1057.34 ng/mg Cre) |
| MPS type VI cats | 1812.78 ng/ml | (1066.34 ng/mg Cre) |
| MPS type VII cats | 3224.61 ng/ml | (1258.63 ng/mg Cre) |

The results obtained from the serum specimens are shown below.

Serum:

| Healthy dogs | 89.1 ng/ml |
| MPS type IIIB dogs | 186.2 ng/ml |
| MPS type VII dogs | 457 ng/ml |
| Healthy cats | 120 ng/ml |
| MPS type I cats | 396 ng/ml |
| MPS type VI cats | 554.4 ng/ml |
| MPS type VII cats | 483.3 ng/ml |

Thus, it has been confirmed that, not only human mucopolysaccharidosis cases, but also urine specimens of animals (non-humans) suffering mucopolysaccharidosis, show significantly high KS level. Moreover, the KS level has been found to be significantly high not only in urine but also in blood (serum). Furthermore, it has been confirmed that mucopolysaccharidoses can be detected not only through the sandwich assay method but also through the inhibition assay method. Particularly, high KS levels in urine and blood (serum) samples from mucopolysaccharidosis type I, III (IIIB), VI, and VII animals are surprising, as such high data have never been expected.

Thus, the above results also show that mucopolysaccharidoses can be detected by correlating the assay results of GAG of a single species (in this case, KS) contained in body fluid (urine or blood) with mucopolysaccharidoses.

EXAMPLE 3

Mass-Scale Detection of Mucopolysaccharidoses

An attempt was made to detect mucopolysaccharidoses in a mass scale by the sandwich method using human urine or plasma as samples. The method is the same as the "(2) Detection of mucopolysaccharidoses through measurement of KS" in Example 1.

Figure 5:
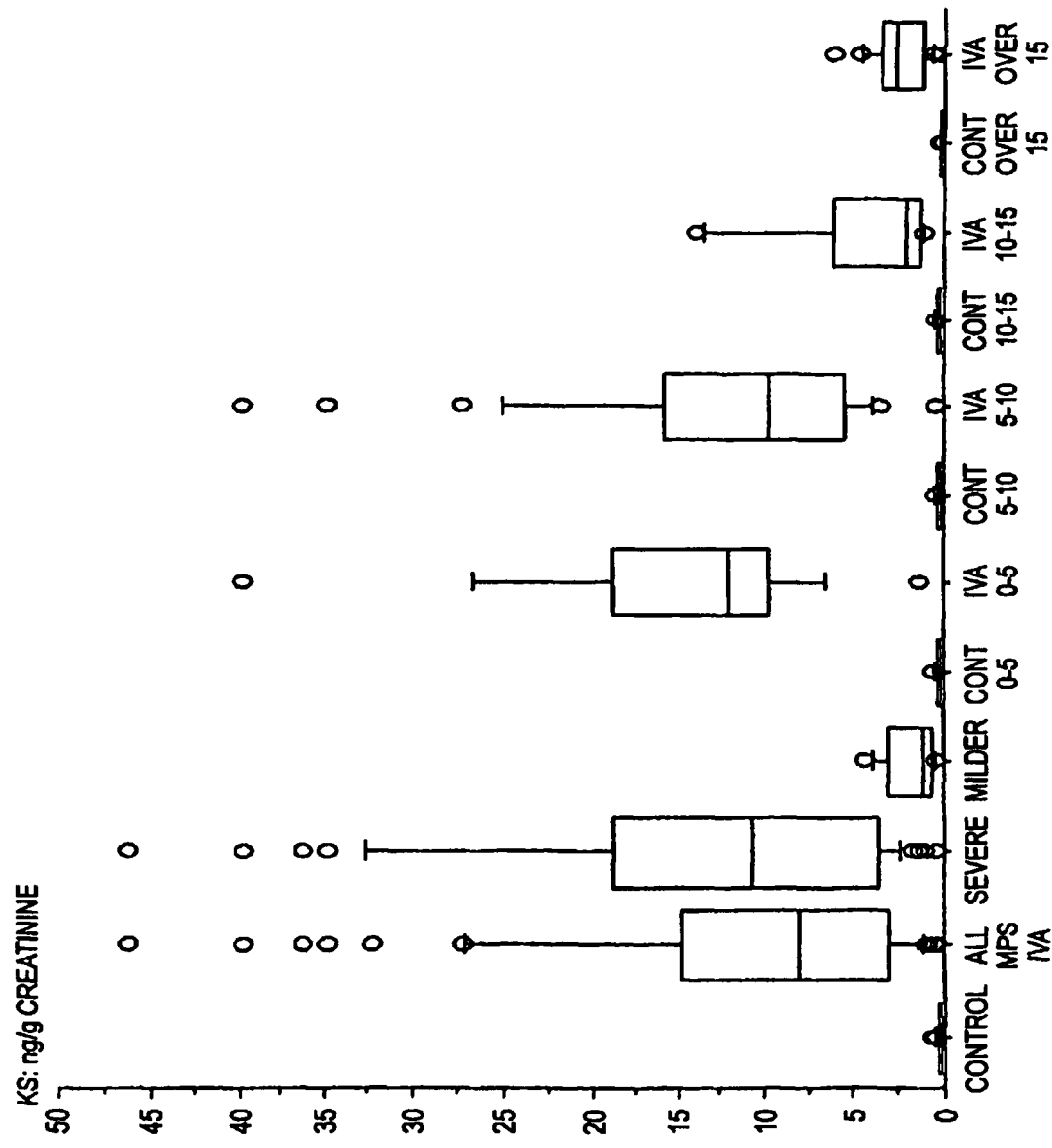
FIG. 5 is a graph showing the KS levels determined in human urine specimens.
Figure 6:
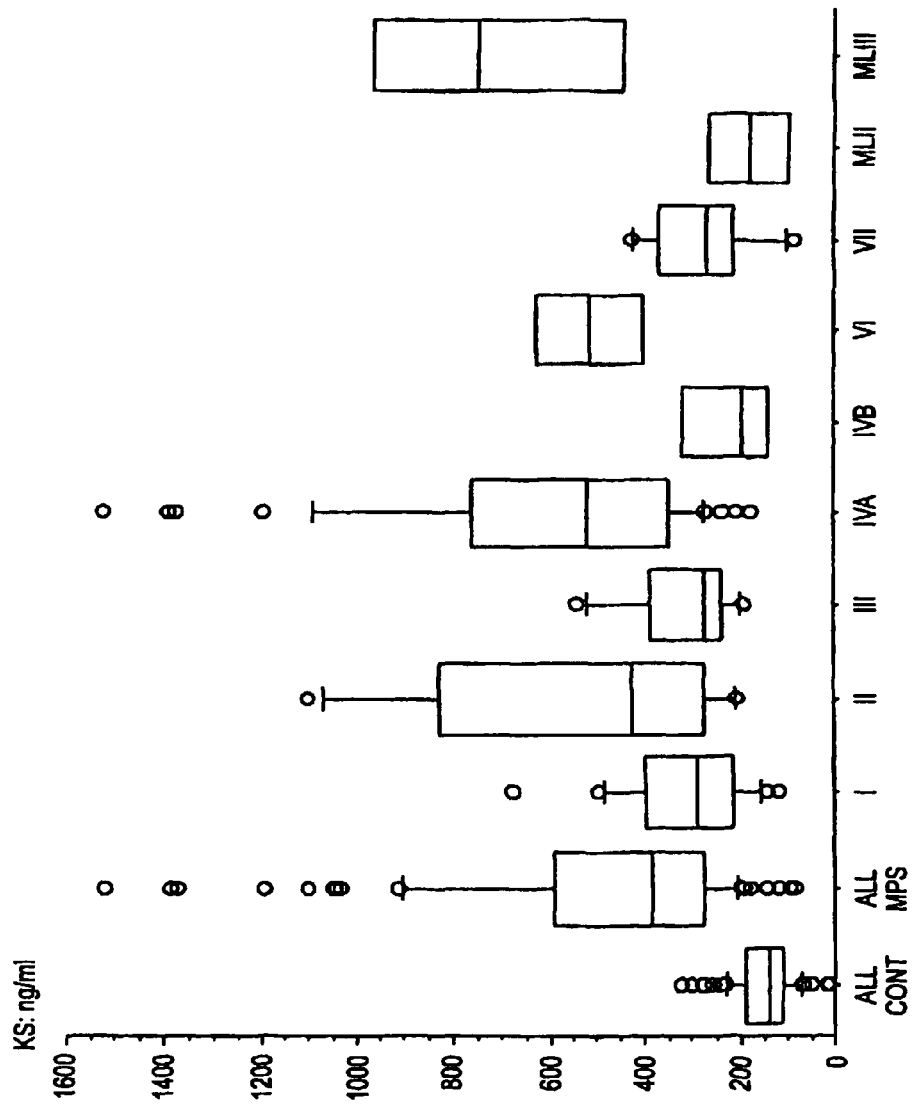
FIG. 6 is a graph showing the KS levels determined in human plasma specimens.
Figure 7:
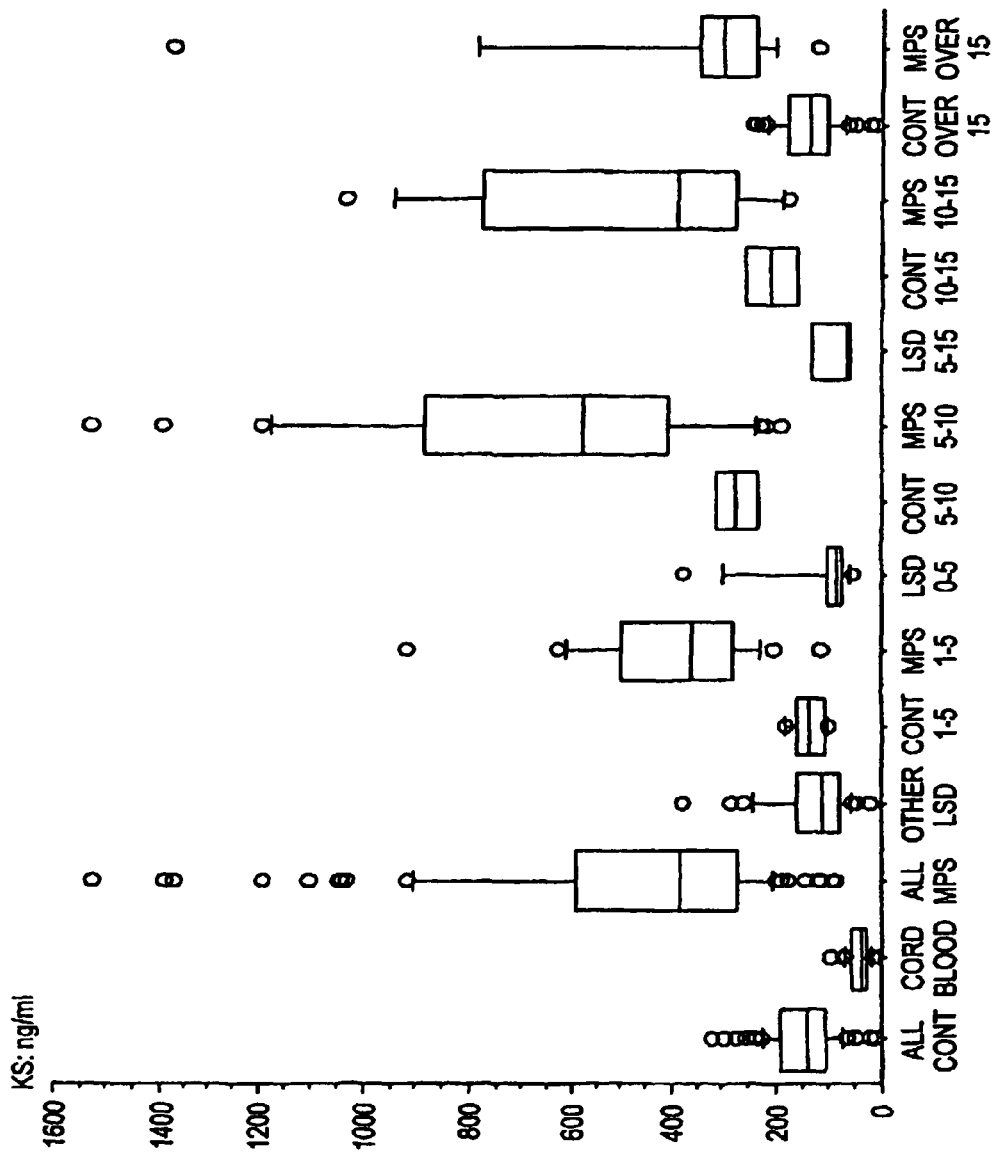
FIG. 7 is a graph showing the KS levels determined in human plasma specimens.

The results of using urine as samples (values corrected for creatinine (Cre) concentration) are shown in FIG. 5, and the results of using plasma in FIGS. 6 and 7.

In FIG. 5, abbreviations show the following results:
Control: result of healthy human (n=67);
All MPS IVA: result of all samples of mucopolysaccharidosis type IVA human (regardless of age, n=78);
Severe: result of mucopolysaccharidosis type IVA (severe type) human (n=54);
Milder: result of mucopolysaccharidosis type IVA (mild type) human (n=11);
Cont 0-5: result of healthy human (from 0 to less than 5 years; n=21)
IVA 0-5: result of mucopolysaccharidosis type IVA human (from 0 to less than 5 years; n=12),
Cont 5-10: result of healthy human (from 5 to less than 10 yearn; n=21);
IVA 5-10: result of mucopolysaccharidosis type IVA human (from 5 to less than 10 years; n=28);
Cont 10-15: result of healthy human (from 10 to less than 15 years; n=10);
IVA 10-15: result of mucopolysaccharidosis type IVA human (from 10 to less than 15 years; n=9);
Cont over 15: result of healthy human (15 years or more; n=29); and
IVA over 15: result of mucopolysaccharidosis type IVA human (15 years or more; n=18).

In FIG. 6, abbreviations show the following results:
All cent: result of healthy human (n=112);
All MPS: result of all samples of mucopolysaccharidosis human (regardless of age, n=88);
I: result of mucopolysaccharidosis type I human (regardless of age, n=17);
II: result of mucopolysaccharidosis type II human (regardless of age, n=11);
III: result of mucopolysaccharidosis type III human (regardless of age, n=7);
IVA: result of mucopolysaccharidosis type IVA human (regardless of age, n=42);
IVB: result of mucopolysaccharidosis type IVB human (regardless of age, n=3):
VI: result of mucopolysaccharidosis type VI human (regardless of age, n=2);
VII: result of mucopolysaccharidosis type VII human (regardless of age, n=6);
MLII: result of mucolipidosis type II human (regardless of age, n=2); and
MLIII: result of mucolipidosis type III human (regardless of age, n=3).

In FIG. 7, abbreviations show the following results:
All coat: result of healthy human (n=112);
Cord blood: result of cord blood;
All MPS: result of all samples of mucopolysaccharidosis human (regardless of age and type, n=88);
Cont 1-5: result of healthy human (from 1 to less than 5 years; n=7);
MPS 1-5: result of mucopolysaccharidosis human (from 1 to less than 5 years; n=19);
Cont 5-10: result of healthy human (from 5 to less than 10 years; n=4);
MPS 5-10: result of mucopolysaccharidosis human (from 5 to less than 10 years; n=27);
Cont 10-15: result of healthy human (from 10 to less than 15 years; n=3);
MPS 10-15: result of mucopolysaccharidosis human (from 10 to less than 15 years; n=12);
Cont over 15: result of healthy human (15 years or more; n=11);
MPS over 15: result of mucopolysaccharidosis human (15 years or more; n=14).

Each of the boxes in FIGS. 5 to 7 shows a range of from 25% to 75% in each group. The bar in each box shows average value. Also, the vertical bars outside the box show a range (a range of from 10% to 90%), and the circles show those departing this range.

EXAMPLE 4

Detection of Mucolipidoses

An attempt was made to detect mucolipidoses by the sandwich method using human serum or urine as samples. The method is the same as the "(2) Detection of mucopolysaccharidoses through measurement of KS" in Example 1.

The results of using urine as samples (values corrected for creatinine (Cre) concentration) are shown below. Regarding the "healthy human", the results are shown as "average value±SD".

Urine:

| | |
|---|---|
| Healthy human | 0.208 ± 0.142 ng/mg Cre |
| ML type II human | 0.92 ng/mg Cre |
| ML type II human | 0.615 ng/mg Cre |
| ML type III human | 1.25 ng/mg Cre |
| ML type III human | 0.75 ng/mg Cre |
| ML (type unclear) human | 0.614 ng/mg Cre |

Also, the results of using serum as samples are shown below. Regarding the "healthy human", the results are shown as "average value±SD".

Serum:

| | |
|---|---|
| Healthy human (cord blood) | 44.2 ± 27.87 ng/ml |
| Healthy human (1-3 years) | 127 ± 23.18 ng/ml |
| Healthy human (4-14 years) | 237 ± 58 ng/ml |
| Healthy human (18 years or more) | 137 ± 51.7 ng/ml |
| ML type II human (0.9 year) | 263 ng/ml |
| ML type III human (12 years) | 1147 ng/ml |
| ML type III human (10 years) | 743 ng/ml |
| ML type III human (40 years) | 340 ng/ml |

It was confirmed from the above results that the amount of KS is markedly increased in animals of not only mucopolysaccharidoses but also mucolipidoses.

Accordingly, it was shown by these results that mucolipidoses can be detected by relating the measured result of a single kind of GAG (KS) in a body fluid (urine or blood) to the mucolipidoses.

EXAMPLE 5

Detection of GM1 Gangliosidoses, Fucosidoses and Galactosialidoses

An attempt was made to detect GM1 gangliosidoses, fucosidoses and galactosialidoses by the sandwich method using human serum or urine as samples. The method is the same as the "(2) Detection of mucopolysaccharidoses through measurement of KS" in Example 1.

The results of using urine as samples (values corrected for creatinine (Cre) concentration) are shown below. Regarding the "healthy human", the results are shown as "average value±SD".

Urine:

| | |
|---|---|
| Healthy human | 0.215 ± 0.14 ng/mg Cre |
| GM1 gangliosidosis human | 3.406 ng/mg Cre |
| Fucosidosis human | 1.44 ng/mg Cre |
| Fucosidosis human | 1.37 ng/mg Cre |
| Galactosialidosis human | 1.18 ng/mg Cre |

It was confirmed from the above results that the amount of KS is markedly increased in animals of not only mucopolysaccharidoses and mucolipidoses but also galactosialidoses.

Accordingly, it was shown by these results that GM1 gangliosidoses, fucosidoses or galactosialidoses can be detected by relating the measured result of a single kind of GAG (KS) in a body fluid (urine or blood) to these diseases.

EXAMPLE 6

Detection Using HPLC

Using human urine as samples, detection of GAG was carried out by an HPLC-aided method (disaccharide analysis). The results are shown in Table 2.

Also, the "Total-CS" in Table 2 shows total chondroitin sulfate, the "DS-4S" shows 4-position-sulfated dermatan sulfate and the "Cre" shows creatinine.

TABLE 2

| Disease | Total-CS (μg/mL) | Total-CS μg/mgCre | DS-4S (μg/mL) | DS-4S μg/mgCre | KS (μg/mL) | KS μg/mgCre | HS (μg/mL) | HS μg/mgCre | Cre (mg/dL) |
|---|---|---|---|---|---|---|---|---|---|
| MPS I | 90.7 | 166.1 | 246.5 | 451.3 | 12.3 | 22.5 | 51.6 | 94.6 | 55 |
| MPS I | 8.6 | 195.6 | 16.8 | 383.5 | 1.1 | 26.2 | 5.1 | 115.7 | 4 |
| MPS II | 40.2 | 77.1 | 91.5 | 175.7 | 6.8 | 13.1 | 46.1 | 88.5 | 52 |
| MPS II | 83.1 | 117.1 | 143.8 | 202.6 | 9.0 | 12.6 | 73.0 | 102.8 | 71 |
| MPS II | 40.4 | 206.4 | 122.0 | 623.0 | 2.7 | 14.0 | 27.5 | 140.2 | 20 |
| MPS III | 7.5 | 81.3 | 2.3 | 25.3 | 1.3 | 13.7 | 18.6 | 202.2 | 9 |
| MPS IIIA | 12.5 | 93.9 | 2.0 | 15.0 | 2.2 | 16.4 | 24.5 | 183.6 | 13 |
| MPS IIIB | 8.3 | 45.3 | 1.5 | 8.1 | 1.6 | 8.6 | 30.0 | 164.6 | 18 |
| MPS IIIB | 20.1 | 54.4 | 2.8 | 7.5 | 2.9 | 7.8 | 81.0 | 219.7 | 37 |
| MPS IVA | 34.1 | 147.9 | 2.9 | 12.4 | 28.9 | 125.3 | 2.2 | 9.5 | 23 |
| MPS IVA | 36.2 | 167.0 | 2.1 | 9.6 | 25.7 | 118.7 | 3.1 | 14.2 | 22 |
| MPS IV? | 175.2 | 333.4 | 4.2 | 8.0 | 56.4 | 107.4 | 5.9 | 11.1 | 53 |
| MPS IVB | 5.5 | 89.1 | 1.7 | 27.7 | 4.1 | 65.7 | 0.3 | 5.1 | 6 |
| MPS IVB | 54.4 | 46.5 | 3.1 | 2.7 | 48.7 | 41.6 | 1.0 | 0.9 | 117 |
| ML II | 22.1 | 233.4 | 1.4 | 15.0 | 3.3 | 34.8 | 1.1 | 11.8 | 9 |
| ML III | 64.4 | 45.2 | 11.3 | 7.9 | 19.4 | 13.7 | 11.1 | 7.8 | 142 |
| ML III | 11.1 | 7.9 | 3.6 | 2.5 | 2.8 | 2.0 | 2.7 | 1.9 | 141 |
| GM I | 5.5 | 59.2 | 0.2 | 2.6 | 5.4 | 58.1 | 0.2 | 2.5 | 9 |
| Fucosidosis | 50.4 | 75.2 | 4.0 | 6.0 | 23.7 | 35.3 | 3.1 | 4.6 | 67 |

TABLE 2-continued

| Disease | Total-CS (μg/mL) | Total-CS μg/mgCre | DS-4S (μg/mL) | DS-4S μg/mgCre | KS (μg/mL) | KS μg/mgCre | HS (μg/mL) | HS μg/mgCre | Cre (mg/dL) |
|---|---|---|---|---|---|---|---|---|---|
| Fucosidosis | 31.6 | 50.7 | 1.5 | 2.4 | 16.6 | 26.6 | 1.7 | 2.8 | 62 |
| Healthy person | 21.1 | 48.7 | 0.3 | 0.6 | 2.5 | 5.8 | 0.4 | 1.0 | 43 |
| Healthy parson | 9.9 | 33.2 | 0.4 | 1.2 | 1.8 | 5.9 | 0.3 | 0.9 | 30 |
| Healthy person | 12.4 | 22.7 | 0.5 | 1.0 | 1.8 | 3.4 | 0.6 | 1.0 | 55 |
| Healthy parson | 30.9 | 18.2 | 1.7 | 1.0 | 3.2 | 1.9 | 3.2 | 1.9 | 170 |
| Healthy person | 12.5 | 7.6 | 0.4 | 0.3 | 0.9 | 0.6 | 0.6 | 0.4 | 164 |

It was shown from Table 2 that the amount of GAG is increased in each disease. Based on this, it was shown that the method of the invention can be carried out also by a method which does not use antibodies.

EXAMPLE 7

Mass-Scale Detection of Lysosomal Storage Diseases

An attempt was made to detect lysosomal storage diseases in a mass scale by the sandwich method using human urine or serum as samples. The method is the same as the "(3) Detection of mucopolysaccharidoses through measurement of HS" in Example 1.

The results of using serum as samples are shown in below. The results are shown as "average value".
Serum:

| Healthy human (n = 51) | 4.89 U/ml |
| MPS type I human (n = 16) | 38.0 U/ml |
| MPS type II human (n = 25) | 82.1 U/ml |
| MPS type IIIA human (n = 6) | 22.0 U/ml |
| MPS type IIIB human (n = 6) | 26.8 U/ml |
| MPS type IIIC human (n = 3) | 13.4 U/ml |
| MPS type IVA human (n = 29) | 7.51 U/ml |
| MPS type IVB human (n = 2) | 9.43 U/ml |
| MPS type VI human (n = 3) | 12.0 U/ml |
| MPS type VII human (n = 5) | 18.9 U/ml |
| MLD human (n = 4) | 9.82 U/ml |
| LIPO human (n = 1) | 103 U/ml |
| TS human (n = 7) | 13.0 U/ml |
| GSD type I human (n = 1) | 19.1 U/ml |
| GSD type II human (n = 1) | 7.57 U/ml |
| Sandhoff disease human (n = 3) | 7.59 U/ml |
| ML type II human (n = 2) | 54.1 U/ml |
| ML type III human (n = 3) | 12.2 U/ml |
| NP type B human (n = 5) | 8.67 U/ml |
| NP type C human (n = 4) | 6.06 U/ml |
| GM2 gangliosidoses human (n = 1) | 10.7 U/ml |
| Krabbe disease human (n = 3) | 6.68 U/ml |
| Fabry disease human (n = 5) | 10.6 U/ml |
| Gaucher disease type I human (n = 5) | 8.18 U/ml |
| Gaucher disease type III human (n = 2) | 11.7 U/ml |

It was confirmed from the above results that the amount of HS is increased in animals of not only mucopolysaccharidoses but also several kinds of lysosomal storage diseases.

Accordingly, it was shown by these results that lysosomal storage diseases can be detected by relating the measured result of a single kind of GAG (HS) in a body fluid (urine or blood) to these diseases.

EXAMPLE 8

Preparation of a Kit of the Present Invention (1)

A kit of the present invention including the below-described components was prepared. The kit can be used to detect mucopolysaccharidoses, etc. through sandwich assay of GAG.

1. 96-well immunoplate, immobilized with 5D4 . . . 1 plate
2. Biotinylated 5D4 . . . 1 vial
3. Avidin-peroxidase . . . 1 vial
4. THE solution . . . 1 vial
5. Reaction stopping solution (1N HCl) . . . 1 vial
6. Washing solution (PBS containing 0.05% Tween 20)
7. Specimen diluting solution (PBS(−) containing 1% bovine serum albumin (BSA))
8. KS standard solutions . . . 1 set Also, another kit of the present invention was prepared, in which a 96-well F58-10E4-immobilized immunoplate and biotinylated F58-10E4 were provided instead of the 5D4-immobilized immunoplate and biotinylated 5D4, respectively.

Also, still another kit of the present invention was prepared, in which a 96-well LY111-immobilized immunoplate and biotinylated LY111 ware provided instead of the 5D4-immobilized immunoplate and biotinylated 5D4, respectively.

Also, yet another kit of the present invention was prepared, in which a 96-well 6-B-6-immobilised immunoplate and biotinylated LY111 were provided instead of the 5D4-immobilized immunoplate and biotinylated 5D4, respectively.

EXAMPLE 9

Preparation of a Kit of the Present Invention (2)

A kit of the present invention including the below-described components was prepared. The kit can be used to detect mucopolysaccharidoses, etc. through inhibition assay of GAG.

1. 96-well immunoplate, immobilized with KS . . . 1 plate
2. 5D4 . . . 1 vial
3. Peroxidase-bound anti-mouse IgG (H+L) . . . 1 vial
4. TMB solution . . . 1 vial
5. Reaction stopping solution (1N HCl) . . . 1 vial
6. Washing solution: PBS containing 0.05% Tween 20 (pH 5.3)
7. Specimen diluting solution: PBS containing 1% BSA and 0.05% Tween 20 WS 5.3)
8. KS standard solutions . . . 1 set While the present invention has been described in detail and with reference to specific embodiments thereof, it will be apparent to one of skill in the art that various changes and modifications can be made therein without departing from the spirit and scope thereof. All references cited herein are incorporated in their entirety.

This application is based on U.S. provisional patent application No. 60/376,194 filed on Apr. 30, 2002 and No. 60/441,326 filed on Jan. 22, 2003, the entire contents of which are incorporated hereinto by reference.

INDUSTRIAL APPLICABILITY

The method of the present invention provides high utility in practice, because it ensures highly accurate, highly sensitive, convenient, rapid, inexpensive detection of lysosomal storage diseases. In particular, since the method enables detection of lysosomal storage diseases through measurement of GAG of only one species, measurement of GAGs of a plurality of species is no longer necessary, thereby attaining improvements in convenience, speed, and cost. The kit of the present invention is of great use, as it facilitates the method of the invention, making its performance more convenient and rapid.

If the present method is performed on all newborn infants to detect potential lysosomal storage diseases in an early newborn stage during which no clinical syndromes of lysosomal storage diseases are manifested, there can be performed enzyme supplementing treatment, genetic treatment, bone marrow transplantation, or similar treatment, to thereby possibly prevent mental retardation, etc.

The present invention is of great use, since it can be used not only for the detection of lysosomal storage diseases but also to grasp the clinical conditions, determine therapeutic regimens, confirm the effects of treatment, observe the pathological course, evaluate pharmaceutical product development, etc.

The invention claimed is:

1. A method for determining the risk of a subject having a lysosomal storage disease comprising:
   detecting the presence of heparan sulfate in a blood sample from a subject suspected of having a lysosomal storage disease that is type IV mucopolysaccharidosis;
   determining a higher risk of the subject having the lysosomal storage disease or diagnosing the subject with the lysosomal storage disease when the level of heparan sulfate detected in the blood sample is elevated compared to a control value of a healthy subject; and
   treating the subject at risk of having type IV mucopolysaccharidosis for type IV mucopolysaccharidosis;
   wherein said treating comprises enzyme replacement therapy, genetic treatment and/or a bone marrow transplant to the subject determined to be at risk for having the Type IV mucopolysaccharidosis.

2. The method of claim 1 that comprises:
   detecting the presence of the heparan sulfate in a the blood sample from the subject suspected of having type IV mucopolysaccharidosis by any one of (i), (ii), (iii), (iv) or (v):
   i) contacting a polypeptide that specifically binds to heparan sulfate with the sample and determining the amount of binding;
   ii) chromatographically detecting the heparan sulfate;
   iii) contacting the heparan sulfate with a dye that specifically binds to it and determining the amount of binding;
   iv) enzymatically degrading the heparan sulfate in the sample, contacting the degraded sample with a polypeptide that specifically binds to heparan sulfate, and determining the amount of heparan sulfate degraded by comparison to a control sample that was not enzymatically degraded; or
   v) detecting the heparan sulfate in the sample by mass spectrometry.

3. The method according to claim 1, wherein the heparan sulfate in said blood sample is in the form of a complex.

4. The method according to claim 1, wherein the subject suspected of having type IV mucopolysaccharidosis is a newborn.

5. The method according to claim 1, wherein detecting the presence of heparan sulfate in the sample comprises contacting a polypeptide that binds to heparan sulfate with the blood sample.

6. The method according to claim 5, wherein the polypeptide that binds to heparan sulfate is an antibody or a polypeptide having a heparan sulfate-binding site of the antibody.

7. The method according to claim 5, wherein the polypeptide that binds to heparan sulfate is immobilized to a solid phase.

8. The method according to claim 5, wherein the polypeptide that binds to heparan sulfate is immobilized to a solid phase and wherein a complex between the polypeptide and heparan sulfate is detected by binding the complex to a second non-immobilized polypeptide that binds to the heparan sulfate.

9. The method according to claim 8, wherein the solid phase immobilized polypeptide and/or the second non-immobilized polypeptide is an antibody or a polypeptide having an antigen-binding site or Fab of an antibody that binds to heparan sulfate.

10. The method according to claim 9, wherein the antibody is anti-heparan sulfate antibody selected from the group consisting of HepSS-1 (mouse, IgM), F58-10E4 (mouse, IgM), HK-249 (mouse, IgM), F69-3G10 (mouse, IgG2b), and JM403 (mouse, IgM); or a polypeptide comprising an antigen binding site or Fab of said anti-heparan sulfate antibody.

11. The method according to claim 8, wherein the second non-immobilized polypeptide is labeled.

12. The method according to claim 1, wherein the detection step comprises:
   contacting a polypeptide that specifically binds to heparan sulfate with a molecule containing heparan sulfate that is immobilized on a solid phase to form a first complex,
   contacting the first complex with the blood sample under conditions suitable for binding of heparan sulfate in the sample to the first complex to form a second complex, and
   detecting any resulting second complex.

13. The method according to claim 12, wherein the polypeptide that specifically binds to heparan-sulfate is an antibody or a polypeptide having a heparan sulfate-binding site of the antibody.

14. The method according to claim 12, wherein any resulting second complex is contacted with a non-immobilized polypeptide that is labeled, and any resulting complex is detected.

15. The method according to claim 14, wherein the non-immobilized polypeptide that is labeled is an antibody or a polypeptide having an antigen-binding site or Fab of the antibody.

16. The method of claim 1, comprising determining the risk of a subject having type IVA mucopolysaccharidosis.

17. The method of claim 1, comprising determining the risk of a subject having type IVB mucopolysaccharidosis.

18. The method of claim 1, further comprising treating a newborn subject for mucopolysaccharidosis type IV by enzyme replacement therapy, genetic treatment, or bone marrow transplantation.

19. The method of claim 1, further comprising separating plasma or serum from a blood sample and detecting the level of heparan sulfate in the plasma or serum.

* * * * *